United States Patent [19]
Passwater et al.

[11] Patent Number: 6,090,414
[45] Date of Patent: Jul. 18, 2000

[54] METHOD AND COMPOSITION TO REDUCE CANCER INCIDENCE

[75] Inventors: Richard A. Passwater, Ocean Pines, Md.; David M. Olson, Minneapolis, Minn.

[73] Assignee: Life Science Labs, Inc., Minneapolis, Minn.

[21] Appl. No.: 08/494,990

[22] Filed: Jun. 6, 1995

Related U.S. Application Data

[63] Continuation of application No. 06/865,639, May 15, 1986, abandoned, which is a continuation of application No. 06/731,593, May 6, 1985, abandoned, which is a continuation of application No. 06/564,184, Dec. 22, 1983, abandoned, which is a continuation of application No. 06/369,986, Apr. 19, 1982, abandoned, which is a continuation of application No. 06/156,080, Jun. 2, 1980, abandoned, which is a continuation-in-part of application No. 05/930,657, Aug. 3, 1978, abandoned, which is a continuation-in-part of application No. 05/806,534, Jun. 14, 1977, abandoned, which is a continuation-in-part of application No. 05/718,469, Aug. 30, 1976, abandoned, which is a continuation-in-part of application No. 05/613,420, Sep. 15, 1975, abandoned, which is a continuation-in-part of application No. 05/593,812, Jul. 7, 1975, abandoned, which is a continuation-in-part of application No. 05/481,788, Jun. 21, 1974, abandoned, which is a continuation-in-part of application No. 05/398,596, Sep. 19, 1973, abandoned, which is a continuation-in-part of application No. 05/271,655, Jul. 14, 1972, abandoned, which is a continuation-in-part of application No. 05/097,011, Dec. 10, 1970, abandoned, which is a continuation-in-part of application No. 05/039,142, May 20, 1970, abandoned.

[51] Int. Cl.$^7$ .......................... A61K 33/04; A61K 38/00; A61K 31/355; A61K 31/34; A61K 31/28
[52] U.S. Cl. .............................. 424/702; 514/2; 514/458; 514/474; 514/492; 514/562
[58] Field of Search .................................. 424/702; 514/2, 514/458, 492, 474, 562

[56] References Cited

U.S. PATENT DOCUMENTS

| | | | |
|---|---|---|---|
| 1,412,873 | 4/1922 | Klein ........................................ | 424/702 |
| 2,832,720 | 4/1958 | Bacher et al. ............................ | 167/81 |
| 2,907,658 | 10/1959 | Luther ....................................... | 99/2 |
| 2,980,588 | 4/1961 | Larde ........................................ | 167/81 |
| 3,184,385 | 5/1965 | Anderson ................................. | 167/81 |
| 3,577,529 | 5/1971 | Pensack ................................... | 424/114 |
| 3,697,287 | 10/1972 | Winitz ........................................... | 99/1 |
| 3,928,578 | 12/1975 | Burns et al. ............................. | 424/702 |
| 4,599,234 | 7/1986 | Amer ....................................... | 424/164 |

OTHER PUBLICATIONS

Can. Med. Ass. V., vol. 100, Apr. 12, 1969, p. 682.
Harman, J. Am. Geriatrics Soc., Aug. 1969, p. 728.
Rodale—The Complete Book of Vit., 1966, pp. 342–348, 352, 353, 359, 367–379, 931–936.
Shamberger—J. Mat. Cancer Inst., vol. 44, No. 4, 1970, pp. 931–936.
Chem. Abst. 64:3292f, 1966.
Chem. Abst. 57: 2793f, 1962.
Chem. Abst. 66:16925d, 1967.
Beckman, J.S., et al., "Nitric Oxide, Superoxide, and Peroxynitrite: The Good, the Bad, and the Ugly", *American Journal of Physiology 271* (*Cell Physiology 40*), C1424–34, (1996).
Clayton, C.C., et al, "Diet and Azo Dye Tumors: Effect of Diet During a Period When the Dye is Not Fed", *Cancer Research*, vol. 9, No. 10, 575–82, (Oct. 1949).
Nelson, A.A., et al., "Liver Tumors Following Cirrhosis Caused by Selenium in Rats", *Cancer Research*, vol. 3, 230–236, (1943).
Shamberger, R.J., "Relationship of Selenium to Cancer. I. Inhibitory Effect of Selenium on Carcinogens", *Journal of the National Cancer Institute*, v. 44, 931–936, (Apr. 1970).
Tappel, "Will antioxidant nutrients slow aging process?", Geriatrics, pp. 97–105, Oct. 1968.
Cameron et al. "Cancer and Vitamin C", published by Warner Books, pp. 183–188, 1979.

*Primary Examiner*—Raymond Henley, III
*Attorney, Agent, or Firm*—Schwegman, Lundberg, Woessner & Kluth, P.A.

[57] ABSTRACT

The five component composition consisting essentially of:
(1) Water soluble antioxidant vitamin C or ascorbic acid, or any of its forms or derivatives, or mixtures thereof.
(2) Oil soluble antioxidant vitamin E or Alpha-tocophorol, or any of its forms or derivatives, or mixtures thereof.
(3) The element selenium, or a chemical (or composition) containing it, or mixtures thereof. The most preferred chemical containing selenium is dimethyl selenide and mixtures thereof. The words "dimethyl selenide" here and hereinafter mean dimethyl selenide and/or it's oxidation products, including dimethyl selenoxide.
(4) A sulfur amino acid, in any form, or a sulfur peptide, or a sulfur protein, or any of their derivatives, or mixtures thereof. The mixture of methionine and cysteine, which contains as impurities some selenomethionine and some selenocysteine, is preferred,—the tripeptide glutathione containing cysteine is also preferred.
(5) Another antioxidant, other than vitamin C and other than vitamin E, which is synthetic or natural and water soluble or oil soluble, or a mixture of such antioxidants, or a combination of such forms thereof. The mixtures of butylated hydroxyanisole and ethoxyquin is preferred.

116 Claims, 1 Drawing Sheet

METHOD AND COMPOSITION TO REDUCE CANCER INCIDENCE

This application is a continuation of application Ser. No. 06/865,639 filed May 15, 1986, now abandoned, which is a continuation of application Ser. No. 06/731,593 filed May 6, 1985, now abandoned, which is a continuation of application Ser. No. 06/564,184 filed Dec. 22, 1983, now abandoned, which is a continuation of application Ser. No. 06/369,986 filed Apr. 19, 1982, now abandoned, which is a continuation of application Ser. No. 06/156,080 filed Jun. 2, 1980, now abandoned, which is a continuation-in-part of application Ser. No. 05/930,657 filed Aug. 3, 1978, now abandoned, which is a continuation-in-part of application Ser. No. 05/806,534 filed Jun. 14, 1977, now abandoned, which is a continuation-in-part of application Ser. No. 05/718,469 filed Aug. 30, 1976, now abandoned, which is a continuation-in-part of application Ser. No. 05/613,420 filed Sep. 15, 1975, now abandoned, which is a continuation-in-part of application Ser. No. 05/593,812 filed Jul. 7, 1975, now abandoned, which is a continuation-in-part of application Ser. No. 05/481,788 filed Jun. 21, 1974, now abandoned, which is a continuation-in-part of application Ser. No. 05/398,596 filed Sep. 19, 1973, now abandoned, which is a continuation-in-part of application Ser. No. 05/271,655 filed Jul. 14, 1972, now abandoned, which is a continuation-in-part of application Ser. No. 05/097,011 filed Dec. 10, 1970, now abandoned, which is a continuation-in-part of application Ser. No. 05/039,142 filed May 20, 1970, now abandoned.

BACKGROUND OF THIS INVENTION

1. Field of This Invention

This invention relates to food and feed supplements. More particularly, this invention relates to food and feed supplements which are effective in retarding or delaying many biochemical and sub-cellular reactions ordinarily associated with the biological degradations which are as a group considered to be the aging process. This invention relates to food and feed supplements which prevent and/or retard all types of cancer (including metastasis) by preventing certain types of oxidation and by alteration of enzyme activity and increaed antibody production. Further, this invention relates to food and feed supplements which are effective in preventing or retarding obtrusive lung disease by the protection of lung membranes from pollution. This invention also relates to food and feed supplements which are effective in preventing the occurrence of and/or retarding atherosclerosis, crib death, muscular dystrophy, radiation illness, xeroderma pigmentosum (here the body damage is slowed), etc. A commonality of all of these biological degradations is the integrity of cellular membranes and their topographical and oxidation-reduction relationships. A major function of this invention is to preserve the membranes, reduce attacks on the membrane by the reduction of extraneous free radicals, to speed repair of membranes and to protect the extra and intracellular components. A second feature, common to the protective mechanisms in several of the above degradations, is the reduction of mis-synthesized proteins caused by altered DNA, and the stimulation of antibodies to destroy the mis-synthesized protein or other agents.

2. Related Art

The following references may or may not be prior art to this invention.

Man does not produce the vitamin C which he needs. Stone, Irwin, "Hypoascorbemia, The Genetic Disease Causing The Human Requirement For Exogenous Ascorbic Acid", Perspectives in Biology and Medicine, Vol. 10, No. 1, (1966); Stone, Irwin, "On The Genetic Etiology of Scurvey", Acta Geneticae Medicae et Gemellologiae, Vol. XV, No. 4, (October 1966).

Biochemical stress causes man to further deplete his ready stores of ascorbic acid. Stone, Irwin, "The Genetic Disease, Hypoascorbemia—A Fresh Approach To An Ancient Disease And Some Of Its Medical Implications", Acta Geneticae Medicae et Gemellologiae, Vol. XVI, No. 1, (January 1967).

The possibility of the use of 25 to 50 grams per day or even higher of ascorbic acid in collogen diseases, such as arthropathies, the rheumatoid diseases and even the aging process, has been suggested. Stone, Irwin, "The Genetic Disease Hypoascorbemia—A Fresh Approach To An Ancient Disease and Some Of Its Medical Implications", Acta Geneticae Medicae at Gemellologiae, Vol. XVI, No. 1, (January 1967).

Stone, Irwin, "The Genetic Disease, Hypoascorbemia", Acta Geneticae Medicae et Gemellologiae, Vol. XVI, No. 1, (January 1967), states much more than one or two grams per day of ascorbic acid would be needed in cancer therapy.

Most daily vitamin dosage levels have been in the milligram range. Some recent sources have recommended large or massive daily dosages of ascorbic levels.

Stone, Irwin, "Hypoascorbemia, The Genetic Disease Causing The Human Requirement For Exogenous Ascorbic Acid", Perspectives In Biology and Medicine, Vol. 10, No. 1, (1966), states that under stress conditions a 70-kg individual would need up to 15.2 grams of ascorbic acid.

Stone, Irwin, "The Genetic Disease, Hypoascorbemia", Acta Geneticae Medicae et Gemelloiogiae, Vol. XVI, No, 1, (January 1967), states that fairly high levels of ascorbic acid should not be toxic.

Rodale, "The Complete Book Of Vitamins", (1966), discloses a 20 percent increase in mouse median life span by adding butylated hydroxytoluene, at the level of 1 to 5 percent of the total diet, to their diet (referring to the work of Harman).

Attention is drawn to: Schwarz, Klaus, "Role Of Vitamin E, Selenium And Related Factors In Experimental Nutritional Liver Diseases", Federation Proceedings, Vol. 24, (January–February 1965), pp. 58 to 64.

Separatum Experientia, 26, 840, (1970), "Vitamin E Deficiency And Chemical Carcinogenesis", states:

"Since vitamin E and intracellular antioxidants are reported to be enriched in tumor tissues as compared to normal tissue, some retardation of tumor induction of tumor growth might be expected in acute vitamin E deficiency. Since the growth of the animals in group 4 was poor, it was difficult to ascribe the decreased size of liver tumors observed in several rats from this group to vitamin E deficiency-alone. Suprisingly, Swick and Bauman have reported that dietary vitamin E decreased the incidence of hepatomas when large amounts of the vitamin were fed after administration of 3-methyl-4-dimethylamino-azo-benzene."

"Miller et al. used a diet containing 0.06% p-dimethylaminoazobenzene and low in vitamin E and have concluded that vitamin E does not exert any effect on the carcino-genicity of p-dimethylaminoazobenzene. Since they used relatively larger rats (initial wt. 180 g vs 60 g used in the present experiment) a lower level of fat (5% vs 10%), a much shorter total period of experimentation (6 months vs 18 months),and did not establish the vitamin E deficiency status. However, the present results, obtained with a different carcinogen (FAA) under more controlled conditions are essentially in agreement with their data. Thus it can be stated that vitamin E deficiency, under the present experimental conditions, does not accelerate the induction or growth of tumors by FAA in rats." [Emphasis supplied][col. 2 2nd and 3rd paragraphs]

So it is seen that the *Separatum Experientia* reference discloses that a deficiency of vitamin E does not accelerate the induction of cancer.

Brewer, Keither A., "Excitation Of The Hydrogen Double Bond", American Scientist, Vol. 56, No. 3, at pages 261 and 263, states that cancer can be induced in the skin by exposure to ultraviolet radiation by penetrating radiation and by long exposure to heat. It also states that carcinogens are complex molecules containing benzene rings with substitutions in the meta position and such compounds can be synthesized from polymers upon excitation by heat, UV radiation, x-rays, α, β and Γ rays and electron bombardments.

Webster, James, "Vitamin C—The Protective Vitamin", Universal-Award House, Inc., (1971), at pages 61 to 64, 154 and 155 deals with vitamin C (ascorbic acid) and cancer. After referring to an article published in the Jun. 21, 1968, issue of "Medical World News", it stated: "* Dr. * advised his patients who have had bladder cancer that the trouble may not come back if they take lots of Vitamin C." [Emphasis supplied] [at page 61, last four lines]. Such statement is only speculative as it uses the word "may". It is also noted that such statement only deals with patients using vitamin C after they have already had bladder cancer. The reference quotes: "He prescribes a gram and a half a day to prevent recurrences of carcinomia of the bladder." [at page 62, lines 3 and 4]. Any positive aspects of such statement is eliminated by the following further quotation: "We have enough circumstantial evidence to warrant a trial of ascorbic acid to prevent recurrences". [emphasis supplied] [at page 62, lines 10 and 11] So such statement, at best, is only an invitation to experiment.

The *Webster* reference, in dealing with the *Medical World News* article, also quotes:

"The Tulane researchers could not demonstrate significant differences in the 24-hour excretion of 3-HOA by bladder tumor patients, smokers and normal patients who were nonsmokers. But they did find much more cinnabaric acid in urine from the tumor patients. And in all three groups, ascorbic acid prevented the formation of this compound." [at page 63, lines 14 to 20]

That is not a statement that large amounts, i.e., 1.5 grams, of ascorbic acid will prevent or cure any type of cancer.

The *Webster* reference, at page 66 lines 9 to 13, states: "* the efficiency of Vitamin C * except for hopeful results concerning bladder cancer."[emphasis supplied] Such statement is only speculative and, at best, an invitation to experiment.

The *Webster* reference, in dealing with an article by E. Schneider in the A.M.A. Journal, quotes: "'A Vitamin C deficiency varying from 3000 to 9000 mg, with an average defiency of 4550 mg was revealed by serial examination with the saturated method performed on ten patients with carcinoma of the stomach, rectum, and uterine cervix and with bronchial carcinoma. In an attempt at improving the general condition of patients with carcinoma before surgical intervention, this Vitamin C deficiency was compensated by daily administration of 1000 to 2000 mg of Vitamin C. Administration of Vitamin C increases the *** defense power but does not exert any anticancerous effect.'" [at page 154, lines 10 to 20] Such statement only states that the "defense power" whatever that means is increased and does not state that large amounts of vitamin C prevent cancer. The phrase "defense power" most likely applies to the normal body defense mechanisms against colds and normal diseases because of the reference of giving the large amounts of vitamin C in "an attempt at improving the general condition of patients with carcinoma before surgical intervention."

The *Webster* reference, in continuing on the Scheider article, quotes a passage that states that daily dosages of 1000 mg of vitamin C and large amounts of vitamin A to various cancer patients helped their general condition, prolonged life and temporarily reduced the size of tumors. Whatever that quotation contains, it does not state that large amounts of vitamin C prevent cancer formation. A further quotation summarizes the entire disclosure in perfect fashion: "'Massive vitamin therapy has the advantage od being free of any risk, since it has no component that may potentially influence tumor development.'" [emphasis supplied] [at page 155, lines 20 to 22] That is another way of saying that high dosages of vitamin C or vitamins C and A are not potential means for preventing the development of cancer.

Georgieff, K. K., "Free Radical Inhibitory Effect of Some Anticancer Compounds", Science, Vol. 173, No. 3996, (1971), pp. 537 to 539, was an attempt to determine whether some typical anticancer compounds were also free radical inhibitors that might block biological reactionsinvolving free radicals. The Georgieff reference, in Table I, shows that at least n-propyl gallate, Mitomycin C, hydroxyurea and vitamin A alcohol have higher free radical inhibition factors than does Vitamin C. Copper compounds are also better. Vitamin C is stated to have little or no anti-tumor activity, but it is supposed to potentiate the activity of other anticancer compounds. The Georgieff reference states: "Vitamin C *. * can act as a reducing agent in redox polymerization systems. Thus, under one set of conditions, L-ascorbic acid can promote the formation of unstable free radicals and under another it can inhibit them. * Ascorbic acid * appears to inhibit various tumors. Glycolysis and repiration of the tumor cells are diminished." [at page 539, col. 1, line 21 to 53] Such statement is speculative and shows that known L-ascorbic acid action is confusing and contradictory. The further speculative nature of the Georgieff reference is shown by the following quotation: "Several ubiquitous compounds (copper, vitamins A and C, and ketoaldehydes), which either suppress the growth of cancer or enhance the carcinocidal effect of other anticancer compounds, show substantial free radical inhibition. Many other natural compounds also appear to be free radical inhibitors as a result of their chemical structures. Most synthetic anticancer compounds that I studied displayed significant inhibitory activity. Thus, free radical inhibitors would appear to play some important role in the biochemistry of the normal cell and in the suppression of cancerous growth." [at page 539, col. 2, lines 8 to 23]

The theory behind the speculations in the Georgieff reference is stated to be: "Previous investigators have found that free radicals are formed when living tissue is irradiated with high energy radiation, and when the dose is sufficiently high, carcinogenesis occurs. The host is often protected with free radical scavengers when being treated with radiation. * the exact role of these free radicals has not yet been established. These observations, as well as those in previous paragraphs, are consistent with the hypothesis that in normal cells there is a balance between unstable free radicals and free radical inhibitors (and their resulting stable free radicals), which probably involves several or many different reactions. An excess of unstable free radicals will tend to induce reactions that will result in carcino-genesis, whereas free radical inhibitors will tend to restore the balance and inhibit cancer. If this hypothesis is correct, the addition of adequate amounts of certain nontoxic free radical inhibitors to the human diet may reduce the incidence of some types of cancer." [emphasis supplied] [at p. 539, col. 2, line 36 to col. 3, line 12]. Even the Georgieff reference states: "Whether my inhibition factors * have any quantitative significance in biological systems has yet to be established." [at p. 537, col. 2, line 47, to col. 3, line 2]—which suggests the use of very low amounts of free radical inhibitors for biological systems.

Feedstuffs, "The Case For Selenite As A Feed Additive", vol. 43, No. 13, p. 12 et seq., states that Se was long ago alleged to be a possible cause of cancer, but speculates that a deficiency of Se or vitamin E may reduce resistance to carcinogen attack.

Feedstuffs, (Apr. 17, 1971), Letters To The Editor, page 10, First Letter, states "* Dr. R. J. Shamberger's discovery of inhibition of experimental skin carcinogenesis in mice by simultaneous skin painting with sodium selenide or vitamin E and croton oil *." It also states that there is an inverse relationship between human cancer mortality and the geographic distribution of Se.

Can. Med. Assoc. J., Vol. 100, (Apr. 12, 1969), Correspondence, page 682, Shamberger Letter, discloses sodium selenide reduced the number of animals with tumors in several carcinogenesis experiments; likewise with animals fed adequate selenium elvels. It also states that there is an inverse relationship between selenium blood levels and human cancer death rates.

The Merck Index, 6th Ed., (1962), page 626, states that methionine is a nutrient, that the recommended daily intake of L-methionine for a normal adult made is 2.2 grams, has been used in fatty infiltration, cirrhosis of the liver and toxic hepatitis, that anorexia nausea and vomiting may occur following large doses, and the oral dosage of DL-methionine was 3 to 6 grams per day.

Chem. & E. News, (Apr. 10, 1972), p. 14, basically teaches that cancer produces or puts out free radicals.

In Harman, Denham, "Free Radical Theory Of Aging: Effect. Of Free Radical Reaction Inhibitors On The Mortality Rate Of Male LAF$_2$ Mice", J. of Gerontology, Vol. 23, No. 4, (October 1968), at page 478, it was reported that no gross tumors were found in mice during an experimental period in which they were fed a daily diet which contained among other things, 20 mg. of α-tocopherol acetate.

Chem. & E. News, (Jun. 29, 1970), "Vitamin A And E Help Maintain Lung Health", states that in one study high dosages of vitamin A, given to benzpyrene-treated hamsters, can inhibit completely the appearance of squamous tumors of the lung. Also, in another study, healthy hamsters, which had been given large dosages of vitamin A for 12 days, had benzpyrene-induced anaplastic tumors from the lungs of hamsters transplanted. It was stated that it was not known from those tests whether there might be a change in cell structure and tumor growth rate.

Harman, Denham, "Prolongation Of Life: Role Of Free Radical Reactions In Aging", J. of the American Geriatrics Society, (August 1969), at page 728, treates the subject of cancer in the title area. Harman, at page 728, lines 13 to 21, states:

"Recently it has been observed that the incidence of mammary carcinoma induced in female white rats by 7,12-dimethyl benz(a) anthracene was higher when the diet contained 20 per cent by weight of corn oil in comparison to the same amount of a saturated fat, coconut oil (31). This result probably is a reflection of a higher rate of lipid peroxidation in the rats fed the corn oil diet, since in a similar experiment in which the base diet was 20 percent by weight of corn oil to which was added either 5 or 20 mg of α-tocopherol acetate per 100 grams of diet, the rats receiving the vitamin-E supplemental diet had significantly fewer tumors (32)."

It is noted that the quotation is directed to showing that a corn oil diet is probably the key to the lowering of the occurrence of tumors and mammary carcinoma.

Mirvish, Sidney S., et al., "Ascorbate-Nitrate Reaction: Possible Means Of Blocking The Formation Of Carcinogenic N-Nitroso Compounds", Science, Vol. 177, (Jul. 7, 1972), at pages 65 to 68, presents chemical data that shows that ascorbic acid blocks the formation of carcinogenic N-nitroso compounds by the chemical reaction between nitrous acid and compounds like piperazine. Urea and ammonium sulfamate were less effective blocking agents. The article suggested the possibility of in vivo formation of carcino-genic N-nitroso compounds from drugs could be lessened by the combination of such drugs with ascorbic acid. The article states "that ascorbic acid might be used for this purpose." [Emphasis supplied].

Most animals synthesize enough vitamin C for their need, but man and other primates do not have the capacity to synthesize vitamin C.

Attention is drawn to: "Symposium Proceedings—The Bio-chemistry, Assay And Nutritional Value Of Vitamin E", Association of Vitamin Chemists, (Mar. 27, 1969); Chem. & E. News, (Aug. 17, 1970), p. 31; Chem. & E. News, (Jun. 29, 1970), pp. 38 and 39; Science, Vol. 169, No. 3945, (Aug. 7, 1970), pp. 605 & 606; Frost Douglas V., Feedstuffs, (Jul. 31, 1971), pp. 11 et seq.; Scott, M. L., International Journal for Vitamin Research, Vol 40, No. 3, (1970), pp. 334 to 343; Chem. & E. News, (Sep. 11, 1972), p. 22; Prevention, (December 1971), pp. 104 to 110; Shamberger, Raymond J., et al., Cleveland Clinic Quarterly, Vol. 39, No. 3, (1972), pp. 119 to 124; Shamberger, Raymond J., Journal of The National Cancer Institute, Vol. 48, No. 5, (May 1972), pp. 1491 to 1497;and Shamberger, Raymond J., Journal Of The National Cancer Institute, Vol. 44, No. 4, (April 1970), pp. 931 to 936.

The convenient preparation of dimethyl selenide is mentioned by Bird and Challenger in "Potassium Alkaneselenonates and Other Alkyl Derivatives of Selenium" in the Journal of the Chemical Society (London) (1942) pages 570 to 572.

The toxicity of dimethyl selenide was investigated by McConnell and Portman and reported in "Toxicity of Dimethyl Selenide in the Rat and Mouse" in the Proceedings of the Society for Experimental Biology and Medicine, Vol. 79 (1952) pages 230 and 231. They found dimethyl selenide to be several hundred times less toxic than all other forms of selenium tested for toxicity, except elemental selenium.

Since the 1942 preparation and 1952 toxicity reports, there does not appear to have been any further investigation of dimethyl selenide for use in man or animal, for any purpose. Nor does there appear to be any suggestion by anyone for further investigation of the use of dimethyl selenide for any purpose. All other known references to dimethyl selenide are as a metabolic product of some other form of selenium. Dimethyl selenoxide, the first oxidation product of dimethyl selenide, would be similar in structure to dimethyl sulfoxide (DMSO), a chemical which has caused considerable controversy.

BROAD DESCRIPTION OF THIS INVENTION

In the biological fields, synergism is not a cumulative effect of the composition which is greater than the sum of the effects of the individual components.

Biological synergism is a concept that the cooperative action of a system is greater than the effect of a system minus one or more of the components. It does not necessarily imply that the cooperative action of the system is greater than the sum of each discrete component acting independently. As an example, biological systems tend to operate within set limits. Compensating mechanisms are usually activated whenever a system varies markedly from normal values.

Low concentrations of vitamin E are easily absorbed by transportation through the intestinal wall in micelles. There comes a point where the micelles become saturated and no more vitamin E can be absorbed. As this saturation point is approached the absorption efficiency decreases. To double the serum tocopherol from that obtained from a dietary intake of 100 mgs per day, more than 500 mgs per day has to be ingested. Intakes above 500 mgs per day are essentially not absorbed. In any event, to increase the absorption beyond the normal limit would be considered biological synergism.

Most biological macromolecules transported in serum do so bound to albumin or other proteins. Various compounds compete for active binding sites on the albumin. It is possible to obtain a desired effect with X units of Compound A and to obtain the same effect effect with Y units of compound B. However, because of a limited number of active binding sites or because of competition-interference effects, XA plus YB does not necessarily yield twice the effect of XA or YB alone or more than the sum of XA acting separately plus YB acting separately. Likewise, 2 times XA will not necessarily double the effect of XA. However, units of compound C may create more active binding sites or reduce competition interference, so XA plus YB plus ZC will yield more than XA plus YB. Biological synergism implies a maximum effect of the system, although the final result is not much greater than the effect of any one of the discrete components. Without the synergism the body could not produce or utilize that extra effect.

Such is the case with the protection of membranes with mixtures of antioxidants. Two antioxidants protect better than one antioxidant, but not necessarily twice as good as either one by itself.

Biological synergism not only involves the maximum saturation or protection possible, but also implies the concept of providing better protection at lesser concentrations, which allows practical applications previously only theoretically possible.

In this invention, not only are the compounds of importance, the reduction in quantities make this regimen possible and are equally as important.

The synergistic effect can thus be measured as how little quantity is required to produce the same improvement or effect. This is opposed to measuring synergism solely by increasing the effect.

One of the components used in the feed supplement of this invention will not give the complete protection provided by the combination. (It should also be noted that the individual also needs a balanced diet to keep up his general health.)

It is impractical to take massive dosages of feed supplements such as going as high as 0.23 percent of body weight. Such massive dosages may lead to body function complications, such as, bowel irregularity, upset stomach, etc. Besides such massive dosages are a waste of money. For example, the feed supplements of this invention do not use more than 20 grams of vitamin E per 120 pounds of body weight, yet get as good as or better results than the use of more massive amounts of vitamin E Yet, more than the micro amounts used in normal nutrition formulations must be used to achieve the utilities of this invention. (It should also be noted that the vitamin E which is not assimilated in the body remains in the stomach, intestines or bladder to combine with or to interface with reactions that produce potential carginogenic materials to protect the body from cancer.)

This invention achieves an increase in life span by usage of practical dosages without toxicity or other side effects resulting from massive dosages.

The food and feed supplement of this invention, because of the effect of any one component on the others, reduces the possible toxicity (and/or side effects) of a single component mechanism. The same or better effect is obtained with a combination of agents resulting in a given level of protection or improvement while not overwhelming the body's normal mechanisms for handling any particular agent. If the mechanism for a given agent is overwhelmed, toxicity is the result. Allagents become toxic after usage of continued large amounts. It is only a matter of quantity (capacity) until a body system is overloaded. Some body systems overload readily with trace elements, such as, selenium; others overload only after considerable quantitites of substances such as tocopherol are absorbed. The food and feed supplements of this invention offer the optimum effect/toxicity relationship due to the synergistic mechanisims of one component offsetting the need for larger quantities of another. The food and feed supplements of this invention also have been developed so that one component reduces the toxic danger of another. Previous teachings would indicated that the toxicity of each agent is strictly additive and not off-setting.

The food and feed supplement of this invention avoids the heavy use of one antioxidant as it uses several antioxidants.

The food and feed supplement of this invention allows a smaller unit dosage to be consumed to achieve a given dosage of improvement, thus becoming a practical formulation. Previous research by another researcher (Harman) showed meager improvement in mean-lifespan with considerably larger quantitites of 0.5 and 1.0 percent of the total diet. Such an amount would be undersirable for animal or long-term usage. The convenient capsule and/or feed additive approach made possible by the five components of this invention allows practical usage on a long-term commercial basis.

The single component (agent) approaches lead not only to saturation effects, but others, such as not treating the entire problem. One agent, e.g., tocopherol may help protect a cellular or cellular-component membrane, but will have little or no effect on circulating free radicals or cellular "ground" substance. Another agent such as ascorbic acid may stabilize the extra-cellular "ground" substance. Another such as butylated hydroxy-anisole (BHA) or ethoxyquin may react with circulating blood free radicals. But no single agent treats each of those problem areas. A combination of agents attack the problem in all areas, at the membrane, within the cell and in the surrounding media (which is the basis of this invention). Agents have been selected which are multi-functional, such as lowering toxicity and stimulating antibodies.

The neutralization of free-radicals in the membrane environment by scavenging with certain antioxidants has not been considered in total by previous experimenters. Reports of large concentrations of a single component selected as to circulate in the blood stream and to randomly interact with circulating free-radicals present in the blood stream have been described (Harman). By reducing the concentrations of free-radicals in the blood stream, membrane damage is lessened. However, there has been no known previous experimentations in regards to preserving the integrity of the viscous extra-cellular material called "ground" substance. [Balazs, E. A., "Chemistry and Molecular Biology Of The Intercellular Matrix", Academic Press, N.Y., (1970).] The "ground" substance is a complex gel containing water, electrolytes, metabolite dissolved gases, trace elements, vitamins, enzymes, carbohydrates, lipids (fats) and proteins. "Ground" substance is rendered highly viscous by an abundance of certain long-chain acid mucopoly-saccharide polymers called glycosaminoglycans and related proteoglycans. Certainly single antioxidants selected for dissolution in blood or bound to blood albumen cannot be expected to effectively prevent liquid peroxidation in the highly viscus ground substance.

This invention concerns a food and feed supplement which contains five critical components, namely:

(1) Water soluble antioxidant vitamin C, or ascorbic acid, or any of its forms or derivatives, or mixtures thereof;

(2) Oil soluble anitoxidant vitamin E, or alpha-tocopherol, or any of its forms or derivatives, or mixtures thereof;

(3) The element selenium, or a chemical containing it, or mixtures thereof;

(4) A sulfur amino acid, in any form, or a sulfur peptide, or a sulfur protein, or any of their derivatives, or mixtures thereof; and (5) Another antioxidant, other than vitamin C and other than vitamin E, which is synthetic or natural and water soluble or oil soluble, or a mixture of such antioxidants, or a combination of such forms thereof.

The most preferred chemical containing selenium is dimethyl selenide and mixtures containing dimethyl selenide. The mixture of methionine and cysteine, which contains impurities some seleno-methionine and some selenocystein, is preferred for component (4), but the tripeptide glutathione containing cysteine is also preferred. The mixture of butylated hydroxyanisole and ethoxyquin is preferred for component (5).

The amounts of the five components range from one milligram to fifty grams for vitamin C, one milligram to twenty grams for vitamin E, one milligram to twenty grams of the total sulfur amino acid containing component, five micrograms to twenty grams for the other antioxidant or total of its mixtures, and five micro-grams to twenty grams of the selenium containing component. The preferred amounts of each, respectively, are 700 mg, 300 mg, 300 mg, 50 mg, and 50 to 500 micrograms depending on the form of selenium. These quantities are one hundred times the amount used in a gerbil test conducted to prove utility. These quantites are also below the maximum amounts now being taken by some humans expect possibly for the other antioxidant component which is, however, unintentionally taken daily as BHA in the form of a preservative for foods in amounts up to 2 mg by significant numbers of people. The selenium amount used in the mentioned gerbil test and specified herein was kept very low, but since dimethyl selenide has such low relative toxicity compared to the other forms of selenium, it could be used at significantly higher dosage and would, by extrapolation, protect from higher environmental carcinogen and pollution exposures.

A benefical product, but one less effective than the five component system specified herein, can be made by leaving out any one (or more) of the five components. This would have less than the optimum synergistic system, but this invention includes a product having less than the five components even though an inferior commercial product results. It is also possible to add components to the five component system without destroying the basic benefical effect of the five components. A deficiency state in some vitamin or nutrient now known to be essential can of course be corrected by adding that specific component to the five components of this invention. For example, if vitamin A was deficient or conditions were created which destroyed the vitamin A available in the diet (pollutants in the air tend to destroy vitamin A in the lungs when inhaled), then vitamin A could be added to the five components. Reduced glutathione, the tripeptide, is normally already present in all types of body tissues and is made by the body from cysteine and methionine. Also, using quantitites of the five components outside of the specific range specified, while inferior, are within the scope of the broader aspects of this invention (the upper limit of the range for selenium can be adjusted depending on the toxicity of the form used, since dimethyl selenide is much less toxic and quickly eliminated from the body). Selenium was recognized as an essential nutrient in 1957, but the amount in food intake depends greatly on the geographical location from which the food was obtained (selenium content of the soil). Vitamin C is a strong reducing agent in biological systems and is commonly taken as a dietary supplement in widely varying amounts by people, but is not manufactured by the human body as it is in almost all other animals. Methionine (and cysteine as a partial replacement) are accepted as essential amino acids.

Among the five components, the optimum quantity of any one component is dependant on, and greatly effected by, the quantities of the other components. The effect is synergistic where one component will tend to spare the other or even replace the other in some but not all functions, and one component will enhance or potentiate the effects of another or others.

Selenium deficiency causes poor growth, fibrotic degeneration, of the pancreas (the organ which produces many enzymes) and a failure of fat digestion due to a decrease in pancreatic lipase and decreased absorption of lipids including vitamin E.

The preferred form of selenium is the reduced selenide form where selenium, which can have $-2$, $0$, $+2$, $+4$, and $+6$ oxidation states, is present in the most reduced $-2$ oxidation state. The body detoxifies the higher oxidation state forms by reducing them to $-2$ and methylating to form dimethyl selenide. Dimethyl selenide is preferred and it can be used in conjunction with other selenium containing compounds. Potassium selenide is water soluble without decomposing, as sodium selenide is stated to do. Zinc selenide and other metal selenides are useful, as well as all organic selenides, and the selenoamino acids. Elemental selenium, while being relatively nontoxic, would be useful to the degree it was absorbed by the body before elimination. Sodium selenite is commonly added to animal feeds to provide selenium, because it is readily available at low cost and easily handled and water soluble. Other selenium compounds, both inorganic and organic, where selenium has positive oxidation states will be changed by the body to more useful forms, so can be used. Thus, any form of selenium that can be taken into the body is within the scope of this invention, but here are definite reasons why all forms fall some where in a preferred order. In addition to toxicity, due to their routes of elimination, (dimethyl selenide is mainly exhaled, but some is eliminated in urine, elemental selenium is fecally eliminated, unless absorbed, and selenite is mainly urine eliminated, but some is exhaled and fecal) multiple forms have advantages.

The sulfur amino acids include all their forns and their peptides and proteins and other derivatives and mixtures, but have a preferred mixture of methinonine and cysteine, plus glutathione.

The antioxidant, other than vitamin C or vitamin E, can be synthetic or natural or mixtures thereof and of any solubility, but should be dispersable throughout body tissues. Non-exclusive examples include butylatedhydroxyanisole and ethoxyquin.

Some forms of selenium are efficient in protecting an organism against the toxic effects of certain metals, such as arsenic, cadium and mercury. These toxic metals react with selenium in an unknown manner to decrease the biological availability of selenium in spite of its increased retention in the organism. The normal synthesis of dimethyl selenide by the body is decreased by these toxic metals. The trace amounts of harmful toxic metals thus play an important role in the pathogenesis of cancer and other diseases by decreasing the biologically useful selenium from the body while possibly increasing the total selenium content. Thus, not only the amount of selenium present in biological material, but the form in which it is present determines its further usefulness in preventing cancer and carrying out its other optimum biological activities. Further, the offspring of organisms exposed to these toxic metals have a much lower selenium content themselves and are thus less able to withstand environment exposure to toxic metals, unless they have some selenium intake themselves.

An important mechanism of the protection provided by this invention was unknown at the time the original application for this invention was filed. The protection mechanism was established in 1974 as being a selenium containing enzyme which acts as a catalyst for the decomposition of peroxides (or hydroperoxides) which therefore prevents the damage the peroxides are known to cause. Lipid peroxidation and free radicals also actually destroy, vital enzymes. The minute amounts of selenium which provide a satisfactory effect are due to the fact that in this mechanism selenium acts as a part of the catalyst enzyme and not as a consumed reactant. There may be other enzyme systems in which selenium is an essential component, and even systems where it is consumed as a reactant, but this invention has demonstrated the net effect of all, unknown systems and those now known, to be a preventative for the formation of cancer, an improvement in the activity and general outward appearance of the animal, and an adtual extension of the animal's useful life. As an extension of the cancer preventative effect, it is possible to combine this effect with any of the current forms of cancer treatment (surgery, radiation, chemotherapy) to prevent a few cancerous cells that are not destroyed by current treatments from spreading (metastasis) to another site where a new cancer could develop.

Dimethyl selenide is also the least toxic form of selenium (other than the elemental form) so it best fits the description of edible as used in this invention. Selenite and the selenoamino acid forms are approximately the same in toxicity, both being several hundred times more toxic than dimethyl selenide.

This invention includes the process of preventing and retarding therosclerosis by the repeated ingestion of the above food and feed supplement, in dosage form. This invention includes the process of preventing and retarding (including metastasis) all types of cancer from all causes by the repeated ingestion of the above food and feed supplement, in dosage form. This invention includes the process of preventing and retarding aging and the effects of environmental pollution by the repeated ingestion of the above food and feed supplement, in dosage form. This invention includes the process of preventing and retarding radiation illnesses (including radiation induced cancer) by the repeated ingestion of the food and feed supplement, in dosage form.

Atherosclerosis involves free-radical reaction with blood vessel wall lipids which form active sites for the deposit of plaque material. The composition of this invention interferes with the free-radical attack on the blood vessel walls, thereby preventing sites for the deposition of plaque material such as fats, cholesterol and calcium. The deposition of the plaque material is not dependent upon their concentrations in the blood stream, nor their molecular form, but entirely upon the existence of active sites on the vessel walls. The greater the number of sites formed by free-radical attack, the more plaque forming material will be removed from the blood stream. Once a mono-layer of plaque covers the sites, ionic attraction increases the deposition of plaque.

Aging represents the progressive changes which take place in a cell, tissue, organ or organism with the passage of time, but is not caused by time itself. Primarily, age changes represent a gradual loss in functional capacity which ultimately results in death of the cell or organism. The aging process begins when there appears to be a loss of communication of information in the DNA/RNA synthetase-protein sequence. The DNA molecule (deoxyribonucleic acid) is part of every cell nucleus. Although the precise mechanism is not agreed upon, the DNA molecule ultimately contains the program for life, aging and death. DNA is believed to be the genetic substance. In this role, it must have two functions: it must contain information in chemical code to direct the development of the cell according to its inheritance and it must be reproducible in exact replica for the transmission of this inheritance to future generations. The RNA molecule (ribonucleic acid) occurs mainly in the cytoplasm of cells and only to a limited degree in the nucleus and is a determining factor in protein synthesis.

When a breakdown of information occurs in the DNA/RNA synthetase-protein sequence, the RNA synthetase is altered and the RNA molecule produced therefrom is changed and is not an exact replica of the parent molecule. The uncontrolled replication of cells in large magnitude is cancer. The protein produced from the altered RNA molecule is therefore mis-synthesized since the component amino acids used are mis-specified or misread by the messenger RNA molecule. When the proteins produced become sufficiently different from the norm, the body senses them as foreign bodies and some may be attacked by antibodies. Meanwhile, the correct proteins required for body maintenance are not being produced as required. The body therefore attempts to increase the speed of protein synthesis to produce the required protein "building blocks", but instead, more and more mis-synthesized or incorrect proteins are produced. Two of the components, tocopherol, and selenium, show synergism in stimulating antibody production. To show the newness and unobviousness of this invention, a spokesman for the gerontological establishement published criticisrn of this concept in the May 10, 1971, issue of *Chemical and Engineering News.* The criticism claimed:

"1) There is not a single published report of experimental evidence which demonstriated that aging is the result of or even accompanied by 'protein mis-synthesis.' Coding errors have been reported to occur, but again, there is not the slighest bit of evidence to suggest that such phenomenom is age-dependent."

"2) There also is not a single published report of experimetnal evidence which demonstrated interference of age-dependent deterioration of physiological function following administration of the 'drugs' included in Mr. Passwater's [the inventor's] formulation." [at p. 9]

Yet, outside confirmation of this particular portion of the inventor's (this) invention was published in the following year [Nature, (July 1972)], when Holliday, R., and Tarrant, G. M., reported that aging human cell lines contain an increasing number of defective enzymes (produced by protein mis-synthesis). The evidence showed that the reason why enzymes become defective in older people, is due to the fact that the greater number of mis-synthesized enzymes break down more easily under heat than perfectly synthesized enzymes. The mis-synthesized enzymes were also shown to be less effective in acting on their substrates.

In September 1972 [Chem. & E. News, (Sep. 11, 1972), page 22] a report was published of G. S. Roth's experiments confirming the existence of an impaired molecular event in DNA synthesis.

Thus, a new approach was reported, rejected by present knoweldge, and later confirmed by independent laboratories. This is the criteria of a new discovery.

One of the inventor's formulations has also been independently tested by A. L. Tappel in terms of reducing age pigment accumulation in the body. Research has shown that progress of the aging process can be monitored by the accumulation in aging body cells of a fluorescent pigment, a protein-lipid complex. The pigment is often called lipofuscin or the "aging pigment".

Tappel, A. L., "Lipid Peroxidation And Fluorescent Molecular Damage To Membranes", in "Pathological Aspects Of Cell Membranes". Vol. 1, Academic Press, N.Y., at page 12, deals with "Membrane Deterioration And Aging Processes" and refers to the inventor's article, Abstra. 23rd Gerontological Society Meeting, October 1970. Tappel confirmed that increased levels of antioxidants and antioxygenic nutrients decreased the extent of lipid peroxidation damage to membranes during aging (the best results resulted from a nutritionally complete normal protein test diet having added, perkilogram, 2.7 gm. of vitamin E, 0.92 gm. of ascorbate, 2.9 gm. of methionine, 2.0 gm. of butylated hydroxytoluene and 0.11 mg. of sodium selenite). This confirms the unobviousness and utility of the inventor's (this) invention.

It has long been theorized that the aging process is a precise genetically programmed mechanism and that alteration of RNA synthetase occurs purely as a function of time. This strict reasoning, however, does not explain acceleration of aging due to environmental pollution which accelerates the physical signs of aging and to mental and environmental stress related phenomena such as anxiety and other emotional stimuli, retirement, illness, avitaminosis, etc.

There has more recently been proposed the so-called "free-radical" theory of aging. Free-radical reactions are so-named because of the transient existence, during the course of chemical reactions, of highly reactive intermediates known as free radicals. The high chemical reactivity of free radicals is due to the presence of a free electron. Free radicals can be detected in very low concentration because of the magnetic moment associated therewith. Free radical reactions occur often in day-to-day life and include smog formation, development of rancidity in butter and other fats, the reaction of oxygen with fuels such as with gasoline in an automobile engine, the drying of oil-based paints and the preparation of conventional plastics. The intermediates, as noted, exhibit high chemical reactivity so that a variety of products may result from these free-radical reactions which are almost invariably irreversible.

In biological systems, therefore, the more or less random and irreversible reactions initiated by free radicals would be expected to produce a multiplicity of deleterious reactions, and research has shown this to be true. The damage produced would also be expected to be greater, for a given rate of reaction initiation, in proportion to reaction chain-lengths. Thus, in the typical free radical reaction of molecular oxygen with organic compounds, for a given rate of initiation:

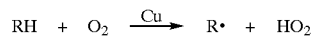

the quantity of RH converted to other compounds depends on the number of times the propagation steps are repeated, i.e., the chain length of the reaction. The complete reaction, in simplified form is as follows:

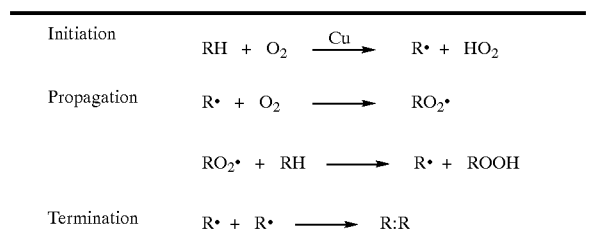

wherein RH is any organic compound and copper is a catalyst. The free radical theory of aging, while reducing the earlier diversity of speculation by accommodating several theories under a single hypothesis, still leaves unexplained the evidence indicating that aging is a genetically programmed, species-specific series of events. Other factors are most likely involved including non-free radical membrane excitation. Thus, while there have been suggested certain single-agent, dietary supplements to retard the aging process, none has been found that approaches total or even substantial effectiveness.

The food and feed supplement of this invention is effective in retarding or delaying a substantial portion of the biological degradation normally associated with the aging process, retarding degradation of RNA synthetase, reducing the accumulation of mis-synthesized cells and protein in the body and stimulating the antibody reaction thereto, combating the aging acceleration effects of stress and stress releated factors, reducing and/or delaying the accumulation of lipofuscin or age pigment in aging body cells, increasing the body's tolerance to radiation and efficiency in utilizing oxygen, establishing and maintaining proper protein synthesis in the body which combats both improper nitrogen balance and poor tissue replacement, inhibiting free radical reactions in the body and helping rid the body of free radicals produced, protecting cell membranes and intracellular membranes from breakdown (membrane stabilization) resulting from free radical attack on the cells, protecting the cellular membranes against the deleterious effects of non-free radical membrane excitation as may be caused by ultraviolet energy absorption, primary radiation interaction, localized thermal energy, carcinogen attack, oxidizing chemicals, etc., preventing and/or retarding cancer, protecting against and preventing muscular dystrophy, protecting against and preventing sudden unexplained infant death (crib death), protecting against and preventing white muscle disease and reducing the damage to the body from the genetic inbalance disease, xeroderma pigmentosum.

The food supplement protects lung membranes by protecting the lung membranes from common oxidizing air pollutants, and protects the vitmain A in the lung membrane from common oxidizing air pollutants.

The mono-acid polyunsaturated lipid components of the lung tissue are degraded by air pollutants, such as, $NO_2$ and $O_3$, into free radicals. The mechanism appears to be one of autoxidation of mono-and polyunsaturates. Also, the natural occurring vitamin A is thought to be critical for the healthy metabolism and growth of epithelial cells of the lung cavities. The common oxidizing air pollutants in effect destroy thevitamin A. The ingestion of the five components of the supplement of this invention protects the natural supply of vitamin A against the common oxidizing air pollutants, as well as protects the membrane lipid components against direct attack.

Muscular dystrophy involves free-radical reactions which alter lysomal topography causing the lysome to rupture and release hydrolytic enzymes into the cytoplasm. This results in tissue cell destruction and the release of the cellular enzymes into the bloodstream (these enzymes are often measured clinically to confirm the presence of muscular dystrophy). The composition of this invention interferes with the free-radical attack and also stabilizes the lysomal membranes.

Xeroderma pigmentosum is a hereditary human disease that can produce skin cancer. Cells of people with xeroderma pigmentosum are defective in repairing ultraviolet radiation damage to DNA.

This invention includes the use of the above food and feed supplement to achieve the utilities specified above and elsewhere herein.

The food and feed supplements of this invention can be added to prepared foods or admixed with foods before consumption of such foods (the same daily consumption of the feed and feed supplements of this invention being needed). This helps to prevent the formation of carcinogens in the food or the digestive tract (e.g., stomach, intestines and bladder).

This invention still further involves a medicament or composition of matter which retards or prevents skin cancer on, at or just under the surface of the skin induced by exposure to ultraviolet radiation, by long exposure to heat and by penetrating radiation. The composition of matter is applied to the exposed portions of the skin (or the portions to be exposed).

Various objects and advantages of this invention are set out above. Still further objects and advantages and the entire scope of applicability of this invention will become apparent to one skilled in the art from the detailed description given hereinafter. It should be understood, however, that the detailed description and the following specific examples are illustrative only.

The supplement is preferably contained in capsules, tablets or pills. If the resulting capsule is too large for ingestion by man and/or animal, the daily unit dosage of course can be placed in more than one capsule, all to be consumed daily so that the daily unit dosage is recieved.

This invention further includes the process of administering the food and feed supplement to animal and/or man, the supplement effectively preventing the occurrence and/or retarding of all types of cancer, including skin cancer. The supplement is preferably administered in capsules, for daily unit dosages.

DETAILED DESCRIPTION OF THIS INVENTION

Figure 1:
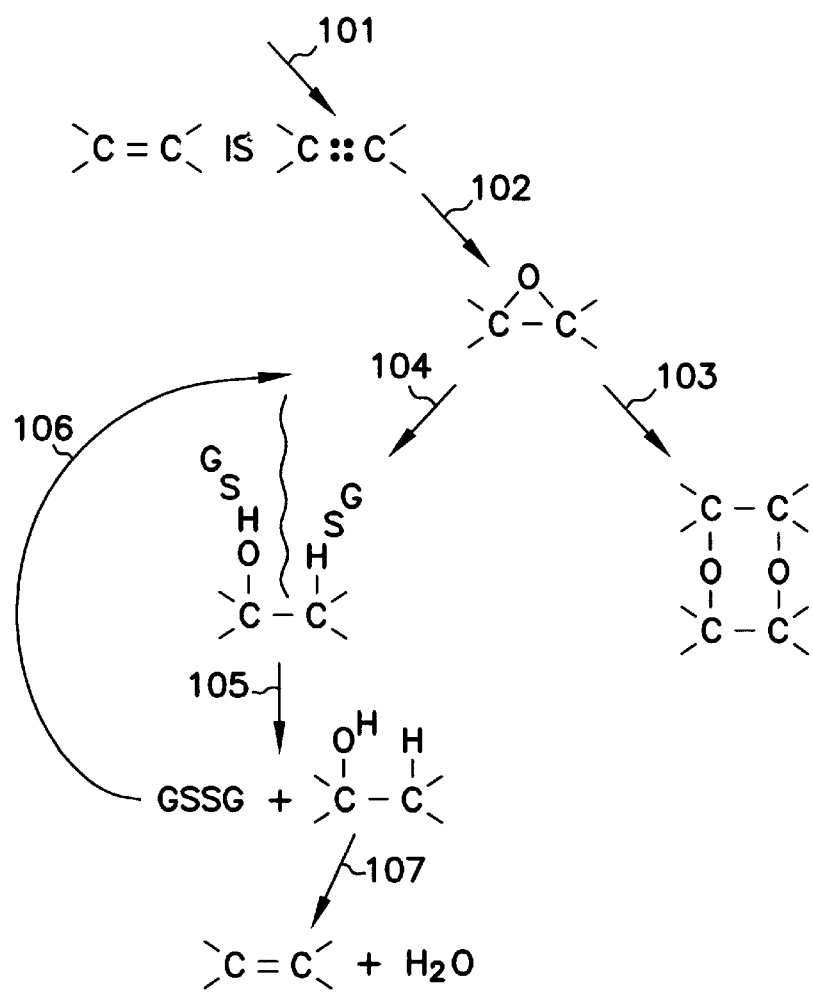
FIG. 1 Illustrates pathways for the oxidation of a double bond to an epoxide and the subsequent repair of the damage by reversion to a double bond.
Figure 1:
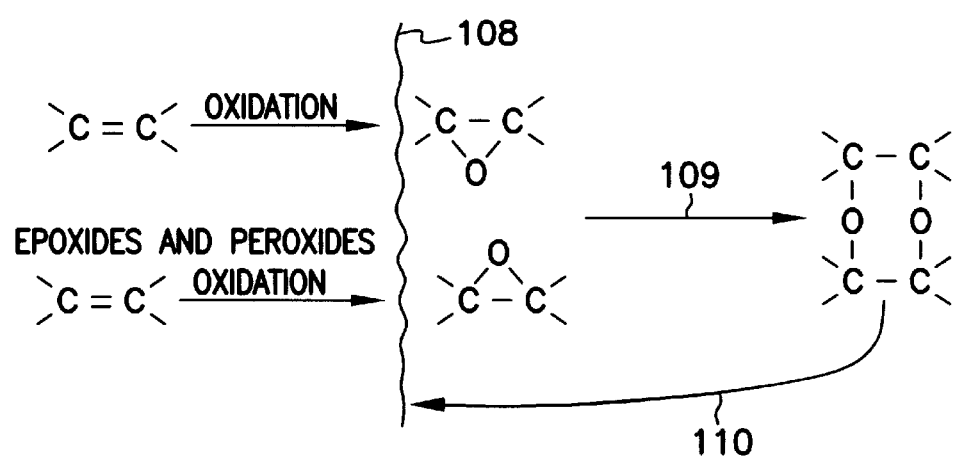

Agents or compounds which protect cell membranes from breakdown resulting from free radical attack on the cells are the membrane stabilizers. The membrane stabilizers protect the cells from free radical attack which would otherwise lead to membrane breakdown and would mean a subsequent leakage of lysosomal enzymes that also damage the DNA molecule. If the cell membrane breakdown goes too far, the situation may go either into cancer or accelerated aging. If the membrane topography is changed from ideal either unchecked growth (cancer) or cellular death (aging) may result. Membrane stabilizers help maintain proper membrane topography and permeability. If the cell membrane is too permeable or not permeable enough, needed nutrients may be lost (aging) or too many may enter (cancer) or needed nutrients may not enter (aging). Cancer begins with a single identifiable event within a cell, and occurs frequently, but it is normally handled by cellular repair and detoxification mechanisms.

The vitamin C, which helps protect lung tissue fat from oxidation by pollutants such as $NO_2$ and $O_3$, acts as a protective antioxidant. From 1 mg to 50 gm daily and preferably about 700 mg of vitamin C is effective within the scope of this invention. The best cell membrane stabilizer is vitamin C. Vitamin C is L-ascorbic acid, namely:

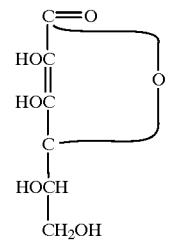

Ascorbic acid is water soluble and is in the solid state at room temperature (melting point=190°–192° C.). The non-toxic salts, esters and derivatives of vitamin C can also be used. Vitamin C forms stable metal salts, such as, sodium ascorbate, which can be used. Sodium ascorbate can be formed by the method described in U.S. Pat. No. 2,442,005. 120 mg. of sodium ascorbate are equivalent in vitamin C activity to 100 mg of ascorbic acid. Sodium ascorbate is water soluble and is a solid at room temperature. Ascorbyl palmitate, calcium ascorbate or sodium erythorbate can be used.

The vitamin E component can be present as a pure compound, preferably alpha-tocopherol, but can also be present as active compounds thereof, for example, the acetate, succinate and other esters, hereafter referred to as tocopheryl. Any of the active isomeric forms including the dl- and d-forms of the compounds mentioned can be used as can natural materials and extracts having vitamin E activity. Examples of useful compounds having vitamin E activity are dl-α-tocopherol, dl-α-tocopheryl acetate, d-α- tocopherol, d-α-tocopheryl acetate, d-β-tocopherol, dl-α-tocopheryl succinate, d-gamma-tocopherol, d-α-tocopheryl succinate, dl-gamma-tocopherol, dl-α-tocopher-amine, d-delta-tocopherol, dl-β-tocophermaine, dl-delta-tocopherol, dl-N-methyl-β-tocopheramine, dl-N-methyl-gamma-tocopheramine, dl-gamma-tocopheramine, α-tocopherol, α-tocotrienol, δ-tocopherol, and β-tocotrienol. Another useful compound having vitamin E activity (it is about 10 times as potent as vitamin E) is the tocopherol metabolite:

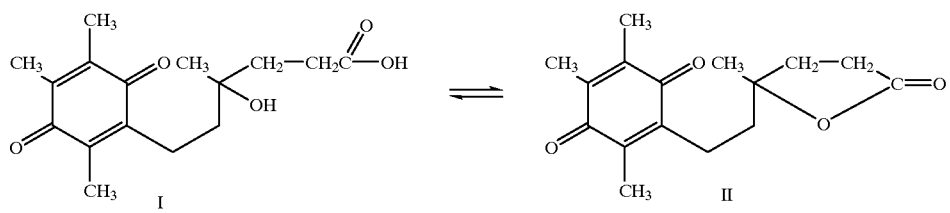

There is no theoretical upper limit to the amount of vitamin E used since the body excretes or stores all excess amounts. As a practical matter, however, daily dosages will contain from 1 milligram to 20 grams, and preferably about 300 mg.

Vitamin E is known as a lipid (edible material) antioxidant and in the body it improves the biological us age of oxygen. This vitamin increases the efficiency of oxygen transfer in the body and also reduces the amount of free oxygen stored therein since it will preferentially react with free oxygen before the various body components. Thus, vitamin E may be used to "preserve" such body components as red blood cells and arterial wall lipids by preferentially reacting with free oxygen or other oxidizing substances which would otherwise attack the body components. Most important and critical from a standpoint of this invention it has been shown that vitamin E exhibits a inique and vital synergistic effect with the selenium-organic (complex known as Factor 3.

The vitamin E may conveniently be added in admixture with a vegetable oil, and particalarly with a seed germ oil such as wheat germ oil, safflower oil, corn oil, soybean oil, etc.

The literature states that the blood becomes nearly saturated with α-tocopherol at about 100 mg. of daily dietary intake, and that massive increases of daily intake are needed to even raise the blood level by small amounts. The literature also states that haemolysis varies with the log of α-tocopherol intake. The food supplements of this invention overcome these limitations of the use of α-tocopherol alone. Selenium increases the absorption of vitamin E by the body.

Knowledge of the trace element selenium as a micronutrient has been developed primarily in the recent years. Its bodily function is in part similar to that of vitamin E in that biochemically it reacts as a lipid antioxidant and as a water soluble free radical scavenger. Practical application of basic nutritional information on selenium has developed rapidly and the element has become a factor of great concern in the nutrition of many commercial animals including sheep, cattle, and hogs. An important, and critical function of selenium in this invention is the formation of the organic complex Factor 3. It has now been found that Factor 3 acts in a synergistic manner with vitamin E as a catalyst to favorably shift the reaction equilibrium toward breakdown of mis-synthesized protein and lipofuscin (the age pigment).

Although theprecise structure of Factor 3 is not known, there is a minimum selenium level required until Factor 3 activity is reached, and also a maximum level after which there is no noticeable increase in Factor 3 activity. In this way, the optimum daily dietary intake from all sources has been shown to be 5 to 10 milligrams. Concentrations that produce measurable Factor 3 activity range from 0.005 to nearly 100 milligrams.

An additional mechanism involving selenium incorporation into the enzyme glutathione peroxidase was shown by another research group in 1973 and 1974. This mechanism helps explain the unexpected synergism.

Selenium, used in conjunction with the dimethyl selenide, may be present in elemental form or as organic or inorganic selenium compounds. It occurs naturally in varying amounts in a wide variety of foods and also is present as an impurity in the natural form of the preferred sulfur-containing amino acids, e.g., with methionine as the compound selenomethionine. This latter is due to the fact that the chemical behavior and reactivity of sulfur and selenium are so similar that it is extremely difficult if not impossible to completely remove selenium from sulfur-containing compounds.

Thus, in food grade sulfur-containing amino acids, the corresponding seleno-amino acid is normally present and thus contains selenium in amounts within the above range. For example, one gram of a commercial food grade sample of cysteine was analyzed and found to contain about 75 weight percent (750 milligrams) of cysteine and contained about 0.1 weight percent (1 milligram) of seleno-cysteine which was roasted to an ash containing about 0.65 milligrams selenium as oxide. Even in research grade sulfur containing amino acids, some small amounts of the seleno forms are unavoidably contained therein.

Thus, the vitamin E, synergistic with the organo-selenium complex Factor 3, is preferably present in minimum dietary concentrations to give optimum synergism. Dietary intake experiments with laboratory animals have indicated that again there are minimum and maximum concentrations of dietary vitamin E required to produce the greatest synergistic effect with Factor 3. Extrapolated to 120 pounds of body weight, it is indicated that of the dietary vitamin E, 50 to 100 milligrams are required for optimum synergistic effect.

Examples of useful edible sulfur-containing amino acids are: cysteine(preferred), methionine, cystine, cystathionine, pencillamine cysteine disulfide, penicillamine, 2-amino-4,4-dimethyl-mercaptobutyric acid, vitamin U, brasinine, djenkolic acid, 2-amino-4-isopropyl-mercaptobutyric acid, 2-amino-4-butyl mercaptobutyric acid, 2-amino-4,4-diethyl-mercaptobutyric acid, dibenzo-yldjenkolic acid, the monohydrochloride of djenkolic acid, the hydrochloride of cystine, 2-amino-2-ethyl-3-mercapto-propanoic acid, 2-thiolhistidine, thiomalic acid, the hydrochloride of cysteine, homocysteine, pantetheine, panthethine, Coenzyme A, and cysteic acid. All isomeric forms can be used.

The sulfur-containing amino acids, proteins, and peptides are normally used in the hydrochloride form or in weak acid or base salt form because they are more readily water soluble.

Peptides contain two or more amino acids held by the amido linkage —NH—CO— or —N=C(OH)— of an amine and carboxyl group.

Examples of useful edible sulfur-containing peptides are: glutathione (a tripeptide of glutamic acid, cystein and glycine, also termed gamma-glutamyl-cysteinyl-glycine), cysteinyl-glycine, and gamma-cysteinyl-methionyl-glycine.

Examples of useful edible sulfur-containing proteins are: keratin, insulin, albumin, ribonuclease, fibroin, collagen and elastin. All of the scleroproteins (albuminoids), some of which are mentioned above, are useful.

The sulfur-containing amino acids are used in this invention in an amount of at least 1 milligram total per daily dosage. Here again, there is no theoretical upper limit since amino acids are foods. For purposes of range in this invention, however, amounts up to 20 grams are specified and about 300 mg are conveniently used. The term sulfur-containing amino acid includes sulfur-containing peptides and sulfur-containing proteins. Cysteine is preferred; but another favored sulfur-containing amino acid, methionine, is also used because of the presence of the methyl group and it is especially effective in counteracting stress related mechanisms which tend to accelerate aging. The sulfur-containing amino acids are sources of sulfur in the body and reduce the effect of radiation in the aging process.

Antioxidants act catalytically to retard or inhibit autooxidation of fats, lipids, polymers, etc. They act chiefly by breaking free radical chains, quenching electron mobility, sequestering, trace metals and scavenging for free radicals. In vivo, antioxidants act to decrease lipoxidase (an enzyme that produces in vivo auto oxidation by initiating free radical chain reactions) capacity by donating electrons or hydrogen radicals to the enzyme, by protonating peroxide-free lipid free radicals on the enzyme surface or by inhibiting free radical formation. The preferred edible synthetic antioxidant is butylated hydroxyanisole (BHA) although any of the synthetic lipid antioxidants can be used such as: 1,2-dihydro-6-ethoxy-2,2,4-trimethylquinoline (ethoxyquin), butylated hydroxytoluene (BHT), 2-mercaptomethyl amine, beta-mercaptoethyl amine (cysteamine or MEA), ubiquinone, tertiary butyl hydroquinone (TBHQ), benzyl isothiocynate, N,N'-diphenyl-p-phenylenediamine (DPPD), butyl paraben, ammonium diethyldithiocarbamate, diethyldithiocarbamic acid, amino ethyl isothiuronium (AET), potassium xanthogenate, bis(ethylxanthogenate) and others with carbon disulfide bonding, thiram, disulfram, alpha-hydroxybenzyl phosphinic acid, para-tertiary-butyl phenol, beta-napthoflavone,quercetin, phenothiazine, propylparaben, 5-methoxy tryptamine, nordihydroguaiaretic acid (NDGA), methylene blue, oxalic acid, citric acid, propyl gallate, methyl gallate, gallic acid, methylglyoxal bis(quanylhydrazone) or methyl GAG, Maneb, tryptamine, tyramine, hydroxyurea, phytylubichromel, 2,5-di-tertiary-pentylhydroquinone, hydroquinone, o-, m- or p-amino benzoic acid (o is anthranilic acid, p is PABA), 2,4-(tris-3',5'-bi-tert-butyl-4'-hydroxybenzyl)-mesitylene, i.e., Ionox 330, aromatic phenols, aromatic amines, vitamin K, other natural antioxidants including the tripeptide reduced qlutathione (GSH), other water soluble antioxidants, etc. The antioxidants can be included in an amount up to 20 grams total per unit dosage, although ordinarily lesser amounts are used with 5 micrograms as the low limit to the range and about 50 milligrams is normal. The reactions of the antioxidants are similar to those of Vitamin E with the important exception that the synergism or complex formation with Factor 3 does not occur.

It has been found that RNA synthetase is altered by at least two related mechanisms. In addition to the highly reactive intermediate free radicals, the alteration may be caused by excited oxygen dimers. Oxygen is taken up and held in all living cells and, is capable of absorbing natural radiation (cosmic ultraviolet, alpha, beta, gamma and X-rays, etc.) and forming excited singlet-singlet or singlet-triplet dimer states. Oxygen normally exists in the triplet state but irradiation can cause triplet-triplet absorption whereby a portion of the oxygen molecules undergo inter-system crossing to the metastable singlet state. The excited dimer persists for as long as 45 minutes and is energetically sufficient to alter RNA synthetase and neurons. Removal of excess available free oxygen from body cells reduces the formation of the excited oxygen dimer by natural or other radiation, thus preserving RNA synthetase. Vitamin E and the synthetic antioxidants of this invention reduce the take-up of oxygen by body cells and also increase tolerance of the body to radiation. The antioxidants also inhibit the rate of free radical initiation and especially in those reactions involving molecular oxygen.

As hereinbefore described, the vitamin E-Factor 3 synergism or complex acts catalytically to favorably shift equilibrium toward breakdown of mis-synthesized protein. The catalyst speeds up reaction involving the sulfhydryl groups of the proteins, especially the formation and breakage of the disulfide bridges within and between peptide chains, and thus presents a mechanism to rapidly cleave incorrect bridges. As a result of the foregoing, the accumulation of mis-synthesized proteins is thus substantially reduced or entirely prevented. The sulfur-containing amino acids serve as a source of materials for body synthesis of glutathione and of sulfhydryl groups which are required to replace the cellular sulfhydryl groups easily oxidized to disulfide bridges and thereby lost in the aging process. Two of the components (tocopherol and selenium) synergistically stimulate the production of antibodies to remove mis-synthesized proteins.

Stress related mechanisms are counteracted in part by the methyl group donor methionine (for choline biosynthesis) thus preventing accumulation of neuro-biosynthesized degradation products and deleterious free radicals. Free radicals have been isolated from the nerve system. They are most probably a by-product of the electrical-chemical nerve impulse mechanism. Thus, stress and nervous activity increase the production of free radicals and thus aging. The onset and development of aging can be monitored in humans by autospy, lifespan measurement and occurrence of initial aging signs such as wound healing, facial wrinkles, loss of endurance and graying of hair. The study of occurrence of initial aging signs is preferred as it is more expedient when dealing with human volunteers.

In an experiment with humans, one group was given one capsule daily of a food supplement of this invention. Another group was given vitamin E alone, and a third smaller group was given conventional "one-a-day" type of supplementary vitamin tablets to serve as placebos. The test was given in a single-blind fashion as the conditions of the experiment did not allow a double-blind experiment.

The groups taking the food supplement of this invention and the group taking Vitamin E only, showed marked improvements in endurance as measured by jogging endurance aid basketball timed endurance experiments.

The group taking the food supplement of the present invention was the only group to show improvements in any of the other categories monitored. Actual improvements in all of the preferred aging indicators were observed by one or more individuals taking the food supplement. One individual (male) showed restoration of hair color, lessening of facial wrinkles, greater endurance, and improved healing of a one cm² wound. Another individual (female) showed a dramatic increase in healing ability as measured by the comparison of a recent child delivery with a former delivery, and comparison with normal healing rates. Both of the deliveries involved surgical procedures. After the earlier delivery, the surgical incisions healed in a normal fashion with incidence of scar tissue. The latter birth occurred after the subject had been taking one capsule of the formulation for about 6 months. The surgical incisions healed in about ⅔rds the time of the first healing, with substantially complete absence of scar tissue and a marked improvement over conditions following healing after the first delivery.

An increase in mental alertness, restful sleep, sense of well-being, improved circulation and reduced heart rates were observed by all taking the food supplement of this invention.

This invention provides a supplement which protects the lung membranes by protecting the natural supply of vitamin A in the lungs against common oxidizing aair pollutants. Examples of common oxidizing air pollutants from which this invention protects the lungs are ozone, oxides of nitrogen, and benzo (a) pyrene.

The food supplements of this invention can be administered in any convenient form, such as, tablets, in digestible capsules, in liquid form, e.g., suspensions, dissolved in solvents. Preferably administration is orally, but can be intraveneously. All of the components of the food and feed supplements of this invention must be in a edible and non-toxic form.

The food supplements of this invention are useful for man and animal. They are normally orally administered. The formulations of this invention can be administered to domestic animals including domestic animals as part of their daily feed ration—the dosages are adjusted according to the body weight of the animal.

This invention includes the discovery that certain combinations and certain quantity ranges of free-radical inhibitors have other valuable effects in addition to retarding senescene. Inhibition of free radicals is described above as delaying the aging process by reducing lipid peroxidation and random free-radical attacks on DNA, RNA, RNA synthetaso, strucutral protein and cellular membranes. A combination of antioxidants was stressed to provide immediate scavenging of free radicals whether they be in aqueous or lipid media. Certain ingredients of those formulations are believed to play additional roles besides antioxidant, free-radical scavenger or radiation protector.

In addition to noting a retardation of the aging process, applicant has observed increased lifespans in experimental animals. The increased lifespan has been primarily due to retarding the deleterious effects of aging. However, the prevention of disease has contributed to increased lifespans.

The absence of cancer and gross tumors in the test animals has been striking in comparison to the controls and what is normally experienced.

The disease prevention has been primarily brought about by preventing carcinogenic materials from exciting viral genomes by free-radical reactions. A secondary mechanism is the preservation of membrane surafce integrity, especially in regard to topography. Free-radical attack at the membrane surface could form topographical "holes" or "gaps" in the distribution of electronic charges, resulting in abnormal cellular chemistry.

The role of food and feed supplements and formulations has been described herein in retarding senescence, protecting against oxidizing air pollutants, and protecting against radiation. Cancer in man and/or animal can be reduced or prevented by the same formulations.

Known carcinogenic substances predictably produce certain types of cancers. The formulations of this invention prevent or reduce the incidence of these cancers whether in or on the stomach, breast, bladder, lung, colon, or other organs, or skin or other noncutaneous portions of the body. The carcinogens are free-radical producers that either destroy membrane topography themselves or activate viral genomes which destroy membrane topography. The formulations of this invention interfere with such process of membrane topography destruction.

A closer look at one of the disease process for cancer will help clarify the multiple aspects of the protection mechanisms of the food and feed supplements described herein.

Carcinogens are generally complex molecules containing benzene rings with substitutions in the meta position. Many polymers and other complex molecules not fitting the description of a carcinogen just described, are actually synthesized into such structures within the body by either biosynthesis or direct excitation by free-radicals, thermal energy, penetrating radiation, etc. See the following mechanism formula:

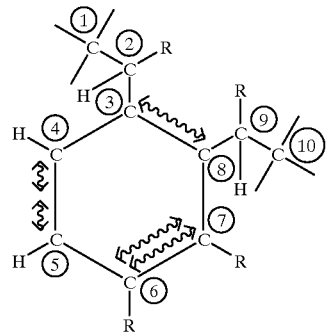

This mechanism formula describes graphically the effect of the induced resonance of the hydrogen atom on the reactions within a polymer. The tetrahedron configuration of the carbon atoms may result in atom C-3 being physically near C-8. Resonance of the hydrogen atoms on C-3 and C-8 will induce penetration into the fields of each other. In consequence, $H_2$ can split off from C-3 land C-8 with the establishment of a linkage between these two atoms. The result is the formation of a closed ring structure. Since the hydrogen atoms on C-4 and C-5 are again in resonance,, $H_2$ will split off to form the double bonds characteristic of the benzene ring. This splitting off of $H_2$ from adjacent carbon atoms is a highly probable reaction. The benzene rings so formed may contain ortho, meta or para substitutions, depending on the positions of the associated R radicals.

This mechanism explains the formation of carcinogens that appear in both the particulate matter and the vapor arising from the pyrolysis of polymers. Again, burned protein such as meat and UV irradiated proteins have been shown in the prior art to be carcinogenic upon subcutaneous injection, whereas normal meats or proteins are not carcinogenic. This mechanism explains cancer induced in the skin by exposure to ultraviolet radiation.

The fact that a non-carcinogenic compound can be converted into a carcinogen is illustrated by 3-hydroxyanthranilic acid (a metabolic intermediate of tryptophan, also called 3-hydroxyanthranilate) which can be readily converted to cinnabaric acid in urine both in vitro and in vivo. The addition of antioxidants and free-radical scavengers to the urine interfere with the conversion of 3-hydroxyanthranilic acid to cinnabaric acid and interferes with the free-radical propagating activity of cinnabiric acid. A water-soluble antioxidant (such as ascorbic acid) alone could preclude the formation of cinnabaric acid, but more complete protection requires a sulfhydryl group from a sulfur containing ingredient such as an edible sulfur-containing amino acid. The sulyhdryl group catalyzes the metabolic oxidation of 3-hydroxyanthranilic acid to α-amino-β-carboxy-muconic acid, thus removing it from possible conversion to the carcinogen, ire., cinnabaric acid. (See p. 365 of *Harper's Review of Physiological Chemistry*, 12th Ed., L. M. Pub. Los Altos, Calif.) The high incidence of bladder cancer in heavy smokers can be explained by the fact that their urine is deficient in ascorbic acid, high in cinnabaric acid, and high in free-radicals and chemiluminescence which probably consumes any naturally occurring free-radical scavengers normally present in the urine.

Free-radicals are in greater concentration in cancers of the liver, uterus, skin and stomach. Protection by a combination of compounds, with one or more present in each aqueous or lipid media, and in body pools, the bladder, and the colon, can concurrently protect against the formation of all types of cancer.

Skin cancer caused by extreme ultraviolet radiation exposure, long heat exposure, nuclear radiation or painting with a carcinogen can be prevented by skin application of the formulations of this invention, or by ingestion of the formulations of this invention. Stomach cancer caused by the ingestion of the carcinogen DMBA [7,12-dimethyl-benz (a) anthracene] can be prevented by first ingesting the food and feed supplement of this invention.

One of the chemical ingredients of this invention by itself will not offer the complete protection provided by the combination. One component may prevent a specific cancer from forming, but only because it has altered the specific mechanism of a specific carcinogen, so that cancer may appear elsewhere because the other mechanisms are not protected by the other components. It is important to first saturate the entire body system with the ingredients of this invention, then continued usage of the ingredients of this invention offers maximum protection against the occurrence of cancer. The supplement of this invention offers far better protection against the occurrence of cancer than known or suggested means and far better retardation of cancer than known or suggested means.

This invention also protects against radiation damage by increasing the body's tolerance to radiation and efficiency in utilizing oxygen.

The supplement of this invention protects against cancer caused by air pollutants such as 3,4-benzpyrene (BP) and benz(c) acridines.

Vitamin C blocks the conversion of some compounds into carcinogens in the stomach and the rest of the digestive tract. Vitamin C is an edible antioxidant and it is also a membrane stabilizer. Glutathione is both an antioxidant and a sulfur containing peptide.

Sulfur-containing amino acids, peptides and proteins protect against carcinogens by chemically tying up the carcinogens or catalysing normal metabolism. Sulfur amino acids can add to the ring sirucutre of the carcinogen, thus altering the K-region and destroying the coplanar molecular conformation and optimum incumberance area required for carcinogenic activity. This is an example of the action of the sulfur-containing ingredient within the scope of this invention. The specific examples given of the sulfur-containing amino acids, peptides and proteins also apply here in addition to glutathione.

A selenium-containing enzyme catalyzes the reduction of peroxides by glutathione by:

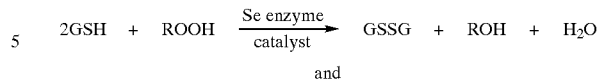

and

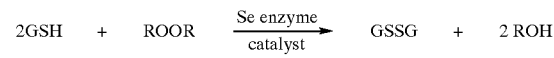

The structure of this selenium-containing enzyme has not been completely determined, but it contains 4 selenium atoms per molecule and has a molecular weight of about 21,000 per selenium atom. This same selenium enzyme, or one similar to it, is believed by applicant to catalyze the reduction of epoxides by glutathione by:

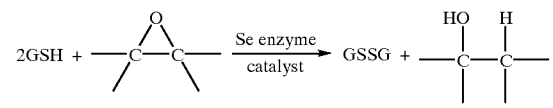

This appears to be the prime mechanism by which cancer is prevented since virtually all known carcinogens have as a common denominator the fact that they activate a covalent double bond which then becomes oxidized to an epoxide. The five components of the food and feed supplement of this invention thus work partially due to glutathione and selenium by an alteration of enzyme activity, by increasing repair of damage to DNA and other molecules' double bonds from environmently caused or natural factors, and by reversing damage not prevented from taking place by the antioxidants. Finally, any damage not prevented or reversed is destroyed by the enhancement of the body's own immune system by the synergistic action of selenium and vitamin E.

The dual and/or supportive roles of each of the five components make the synergistic effects which results an improvement of both the quality and duration of body processes.

The gradual deterioration, called aging, is believed due partially to forming crosslinkages by the two reactions:

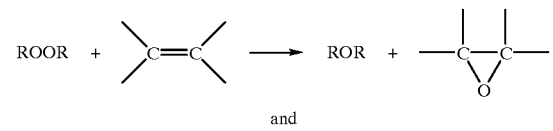

and

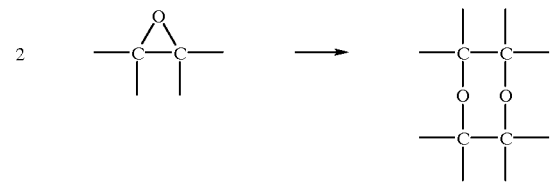

Cross-linkages damage the cell so that normal function is decreased and the cell can no longer undergo normal cell division. This is one mechanism by which peroxides can damage any normal double bond structure.

Carcinogens make the reactions easier, more rapid, more likely to occur, and more widespread by activating the double bond so it is more reactive and susceptible to conversion to the epoxide.

As illustrated in FIG. 1, carcinogens are electrophyllic (including R free radicals) substances that seek electron rich areas. Carcinogen seeks to activate double bond (covalent) which becomes oxidized at 101; Antioxidants prevent peroxides and epoxides formation at 102; Crosslinking causes aging and cancer if the carcinogen has attacked DNA or RNA, crosslinking prevents normal function of DNA or RNA in transfering code to build new cells; this results in uncontrolled growth of abnormal cells at 103; GSH is glutathione, Se enzyme catalyst; GSH reacts as Se enzyme breaks epoxy bond at 104 and 105; Regenerated by vitamin C and biological reducing agents at 106; Normal body process gives original double bond at 107; Antibodies destroy incorrectly formed chemicals recognized as foreign; prevent oxidation by use of specific antioxidants at 108; Cross link epoxides at 109; and reverse oxidation damage by Se enzyme catalyst and glutathione to prevent crosslinks at 110.

One of the main uses of selenium is as an electronic semiconductor (conducting electrons only under certain conditions) in making electronic components such as transistors, diodes, etc. In a sense, it may serve the same biological purpose in an organism, acting like a semiconductor by supplying electrons at times but only under certain conditions.

Since the common denominator of the ultimate reactive metabolites of carcinogens is their electron deficient status which causes them to react with the electron rich sites in cellular nucleic acids and proteins, a semiconductor effect within the carcinogen area should lessen the destructive reactions to the DNA (deoxyribonucleic acid) which change the structure of the DNA and cause the cell to function abnormally. Regardless of the site or the specific carcinogen, the uncontrolled growth of abnormal cells is what characterizes what is termed cancer, so the salient question becomes: What can be used to prevent changes in the structure of DNA as it directs cell replication and what enhances the body's own immune system to repair (by breaking down to basic components and reforming) the incorrectly structured DNA.

Anything that could be used to prevent the incorrect structure replication, should thereby not only control the gross abnormalities called cancer, but logically leadsto various general improvements in the function during their lifespan for all the cells of the body (particularly those of the vital organs) and the attainment of their maximum life span even under conditions of stress from chemical carcinogens or other toxic pollutants which effect the body by their action on DNA structure.

The basic approach is a logical one: start with a functionally useful molecule, then (1) try to prevent it from being oxidized to any harmful form and (2), what cannot be prevented from being so oxidized, one tries to reverse once the oxidation has taken place to restore the molecule to its functionally useful, preoxidized form, and (3), if functional restoration cannot be accomplished, one wants to destroy the harmful form, as a last resort, so that the molecule if it can no longer do any good, will at least do no harm. The big problem is how to accomplish these specific goals. The supplement of this invention works by causing the desired results with an extremely small dosage daily and favorable, if any, side effects without toxicity. The toxicity is so low that the amount of dimethyl selenide used could easily be increased when there was reason to believe that extremely harmful environmental factors had been encountered (or were anticipated immediately).

There are at least three effects which combine synergistically from the components used in this invention:

(1) The antioxidant effect of preventing epoxide and peroxide formation (for both water and oil soluble media).

(2) The selenium enzyme activity enhancement effect which actually makes the reversal of peroxide and epoxide formation possible by the catalysis of the glutathione reaction to destroy and convert peroxides and epoxides which have formed into hydroxide and hydrogen forms and return the basic molecule to its original preoxidized useful form.

(3) The synergistic vitamin E and selenium increase in antibody formation effect on the body's own immune system (for example, here 1+7=35).

Also vitamin C, as a good biological reducing agent, tends to keep the selenium present in its most effective and least toxic oxidation state. Methionine not only reduces selenium toxicity as a methylating agent, but together with cysteine is a precursor of glutathione.

The edible antioxidants, among other things, break free radical chains, quench electron mobility and scavenge for free radicals. In vito, antioxidants act to decrease lipoxidase (an enzyme that produces in vivo auto-oxidation by initiating free radical chain reactions) capacity by donating electrons or hydrogen radicals to the enzyme, by protonating peroxide-free lipid free radicals on the enzyme surface or by inhibiting free radical formation.

Antioxidants, as used herein, includes both water soluble and/or lipid antioxidants other than vitamin C and vitamin E, whether natural or synthetic.

Examples of useful synthetic lipid antioxidants are: BHA, ethoxyquin BHT, TBHQ, MEA, thiram, GSH, etc.

The supplement contains enough natural or synthetic water soluble or lipid antioxidant for consumption of between 5 micrograms and 20 grams thereof, per day.

Examples of useful edible natural lipid antioxidants are GSH, ubiquinone, lecithin, cephalin and vitamin K. Some of the natural antioxidants may be prepared synthetically, but they are treated herein as natural antioxidants. Other useful edible natural antoixidants are 2,3-dimethoxy-5-methylbenzoquinones having polyisoprenoid side chains at the number six carbons, and the following quinols:

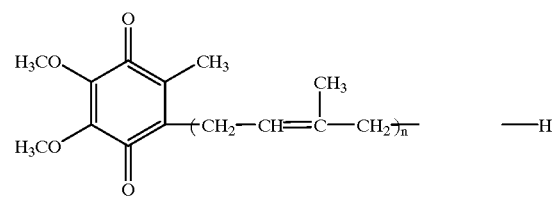

where n=4 to 12, and

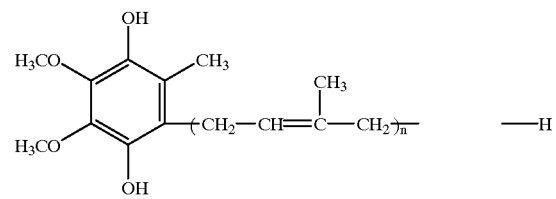

where n=4 to 12.

Vitamin E is a natural antioxidant but its usage, by weight, differs slightly with the activity of the form used. The supplement contains enough vitamin E, for consumption of between 1 milligram and 20 grams thereof, and preferably 300 milligrams thereof, per day.

The vitamin E component may be present as a pure compound, alpha-tocopherol, but can be beta-tocopherol, delta-tocopherol or gamma-tocopherol. The vitamin E component may also be present as active compounds thereof, for example, the acetate, succinate and other esters. Compounds, such as, tocopherylquinone, can be used. Any of the natural or synthetic active isomeric forms including the d-, dl- and l- forms of the compounds mentioned may be used as may natural materials and extracts having vitamin E activity. There is no theoretical upper limit to the amount of vitamin E used since the body excretes or stores all excess amounts.

Vitamin E is known as a lipid antioxidant and in the body reduces the biological need for oxygen. This vitamin increases the efficiency of oxygen transfer in the body and also reduces the amount of free oxygen stored therein since it will preferentially react with free oxygen before the various body components. So vitamin E may be said to "preserve" such body components as red blood cells and arterial wall lipids by preferentially reacting with free oxygen or other oxidizing substances which would otherwise attack the body components. Most important and critical from a standpoint of the present invention, it has been shown that vitamin E exhibits a unique and vital synergistic effect with the selenium-organic complex known as Factor 3.

The vitamin E may conveniently be added in admixture with a vegetable oil, and particularly with a seed germ oil such as wheat germ oil, safflower oil, corn oil, soybean oil, etc.

The food and feed supplement of this invention includes selenium. The selenium can be present in elemental form and/or as all other organic or inorganic selenium compounds. The selenium is used in an amount between 5 micrograms and 20 grams, and preferably 50 to 500 micrograms depending on the form used, per day. Dimethyl selenide can be used in a higher dosage if there is large exposure to carcinogens or toxic substances because it is relatively non-toxic compared to other forms of selenium.

Because lung cancer is one of the most common and fatal types of cancer, the use of a volatile form of selenium like dimethyl selenide makes sure that the protection is delivered to the lungs in a usable form. The body converts most other forms of selenium to dimethyl selenide, but this form improves efficiency of utilization of the full amount administered. Elemental selenium may not be utilized to any significant degree before being eliminated from the body in other ways than through the lungs. Selenite is converted to a volatile form to a greater degree but is more toxic than elemental selenium so a smaller dose must be administered (same for selenocysteine and selenomethionine). This may all sound very simple now because it is so logical, but applicant does not know of any previous research which suggests or even mentions the use of dimethyl selenide to prevent cancer as something to be investigated, let alone actually performing any experiments.

The reaction of carcinogens with the cell components may produce free radicals or peroxidize lipid membranes. The main reaction of polycyclic hydrocarbons appears to be oxidation by hydrogen peroxide or an oxygen atom to activate double bonds, to yield intermediary epoxides. Peroxidation may damage cells in several ways. Antioxidants inhibit early-critical oxidation, but selenium actually reverses oxidation that has taken place, to form peroxides or epoxides, by converting the bonding to hydroxides (and then conversion to double bonds are possible by normal body processes). Enzyme destruction, itself, can take place via lipid peroxidation and free radicals.

Selenium occurs naturally in varying amounts in a wide variety of foods and also is normally present as an impurity in the sulfur-containing amino acids, e.g., in methionine as the compound selenomethionine. This latter is due to the fact that the chemical behavior and reactivity of sulfur and selenium are so similar that it is extremely difficult if not impossible to completely remove selenium from sulfur containing compounds. Thus, in food grade or edible sulfur-contaning amino acids, the corresponding seleno-amino acid is normally present and thus contains selenium in amounts within the above range. For example, one gram of a commercial food grade sample of cysteine was analyzed in the prior art, and found to contain about 75 weight percent (750 milligrams) of cysteine and contains about 0.1 weight percent (1 milligram of) seleno-cysteine which was roasted to an ash containing about 0.65 milligrams of selenium, as oxide. Even in research grade sulfur-containing amino acids some small amounts of the seleno form are unavoidably contained therein.

Examples of useful edible selenium compounds are dimethyl selenide (preferred), all other organic and inorganic selenides (potassium selenide preferred), selenocysteine, selenomethionine, the selenium oxides, selenoglutathione, selenocysteine and the organo-selenium complex Factor 3 which is described inapplicant's prior application Nos. 39,142 and 97,011. Forms of selenium in its most reduced −2 oxidation state are preferred.

Other nutrients, fillers, vitamins, solvents, etc., can be added to the food and feed supplements of this invention which may be segregated or together for ingestion.

All of the specified range amounts of components and preferred amounts set forth herein are based on the active component, so salts, etc., thereof would be used in correspondingly larger amounts.

This invention is useful in the treatment of man and animal.

The components of the supplement of this invention are definitely synergistic and each component participates in at least two of the three effects previously described (antioxidant, enzyme activity enhancement and increase in antibody formation by a stimulated immune system). As the components are interrelated, one sometimes is able to substitute for another, and one is always aided in function by another, providing synergism.

The complex, interwoven, synergistic process can be simply stated as: Antioxidants prevent peroxide formation, then the selenium containing enzyme glutathione peroxidase prevents peroxide conversion to epoxide and reverses any epoxide formation that has taken place, and antibodies destroy anything that is damaged and not repaired so that it is not recognized as normal.

More simply, antioxidants prevent peroxides, the selenium enzyme prevents and reverses epoxides, and antibodies destroy foreign remains.

In prior disclosures, other illustrative ranges of the ingredients of this invention are: antioxidant, 10 to 2000 mg or 10 to 1000 mg or 10 to 500 mg or 10 to 100 mg or 0.1 to 500 mg or 5 to 50 mg or 1 to 100 mg or 0.01 to 500 mg (0.01 mg=10 micrograms) or 1 microgram to 100 mg, per 120 pounds of body weigh per day (giving minimum and maximum range of 1 microgram to 2 g); selenium, calculated as oxide, 0.01 to 100 mg or 1 to 10 mg or 0.5 to 10 mg, per 120 pounds of body weight per day (minimum and maximum 10 g to 100 mg); sulfur-containing amino acid, 100 to 2000 mg or 200 to 400 mg or 100 to 5000 mg or at least 25 mg or 100 to 500 mg, or no upper limit, per 120 pounds of body weight per day (minimum and maximum 25 mg to greater than 5 g); vitamin E, 20 to 2000 mg or 250 to 1000 mg or 10 to 500 mg or 10 to 100 mg or 30 to 2000 mg or 10 to 1000 mg or 10 to 10 g or 50 to 100 mg or 500 to 1 g or about 50 to about 1,000 mg or 5 to 2,000 mg, or no upper limit, per 120 pounds of body weight per day (minimum and maximum 10 mg to greater than 10 g); and vitamin C, 100 to 5000 mg or 250 to 2000 mg or 200 to 5000 mg or 10 to 5000 mg, per 120 pounds of body weight per day (minimum and maximum 10 mg to 5 g).

The objects and the entire scope of applicability of this invention are readily apparent to one skilled in the art from the general detailed description given herein. It should be understood, however, that the detailed description and the following specific examples are illustrative only.

The following specific examples are indicative of optimum and preferred food and feed supplement formulations in accordance with this invention. In each case, the mixture was prepared and placed in one or more size 0 or larger gelatin capsules depending upon the final bulk of the mixture. In all of the examples, the sulfur-containing amino acid was research-grade unless otherwise specified. In all of the examples, unless otherwise specified, parts and percentages are by weight.

EXAMPLE 1

A mixture containing 1 gram of methionine, 1.0 milligram of selenomethionine, 2 grams of butylated hydroxytoluene and 2 grams of ascorbic acid (vitamin C) was divided into 10 equal portions and compressed into tablets. Each tablet was added cc a gelatin capsule containing 0.5 gram of alpha-tocopherol. Each completed capsule contained about 0.1 gram of methionine, 60 micrograms of selenium (measured as oxide), 0.2 gram of butylated hydroxytoluene, 200 milligrams of vitamin C and 0.5 g. (500 I.U.) of vitamin E. A completed capsule was taken daily by an adult human.

EXAMPLE 2

A mixture containing 1 gram of methionine, 1.0 milligram of selenomethionine, 1 gram of butylated hydroxytoluene, 1 gram of ascorbic acid (vitamin C), 1 gram of lecithin and 20 micrograms of vitamin $B_{12}$ was divided into 10 equal portions each of which was compressed into tablet form. Each tablet was added to a gelatin capsule which already contained 0.4 gram of alphatocopherol. Each completed capsule contained about 0.1 gram of methionine, 60 micrograms of selenium (measured as oxide), 0.1 gram of butylated hydroxytoluene, 100 milligrams of vitamin C, 0.1 gram of lecithin, 2 micrograms of vitamin $B_{12}$ and 0.4 gram (400 I.U.) of vitamin E. A completed capsule was taken daily by an adult human.

EXAMPLE 3

A mixture containing 1 gram of cysteine, 1.0 milligram of selenomethionine, 0.1 gram of butylated hydroxytoluene and 2.0 gram of ascorbic acid (vitamin C) was divided into 10 equal portions and compressed into tablets. Each tablet was added to a gelatin capsule already containing 50 milligrams (50 I.U.) of vitamin E. Each completed capsule contained about 0.1 gram of cysteine, 0.1 milligrams of selenomethionine equivalent to 60 micrograms of selenium (measured as oxide), 10 milligrams of butylated hydroxy toluene, 200 milligrams of vitamin C and 50 milligrams (50 I.U.) of vitamin E. A completed capsule was taken daily by an adult human.

EXAMPLE 4

A mixture containing 1.0 gram of food grade cysteine, 100 micrograms of butylated hydroxytoluene and 2.0 grams of ascorbic acid (vitamin C) was divided into 10 equal portions and compressed into tablets. Each tablet was added to a gelatin capsule already containing 500 milligrams of vitamin E. Each completed capsule contained about 0.1 gram of cysteine, 10 micrograms of butylated hydroxytoluene, 64 micrograms of selenium (as oxide present as an impurity in the food grade cysteine), 200 milligrams of vitamin C and 500 milligrams of vitamin E. A completed capsule was taken idaily by an adult human.

EXAMPLE 5

Example 4 was repeated with the exception that each capsule originally contained the 500 milligrams of vitamin E in admixture with 1 gram of wheat germ oil. A completed capsule was taken daily by an adult human.

EXAMPLE 6

A mixture containing 1 gram of cysteine 1.0 milligram of selenomethionine, 0.1 gram of butylated hydroxytoluene and 0.5 gram of sodium ascorbate was divided into 10 equal portions and compressed into tablets. Each tablet was added to a gelatin capsule already containing 500 milligrams of vitamin E. Each completed capsule contained about 0.1 gram of cysteine, 0.01 milligrams of selenomethionine equivalent to 60 micrograms of selenium (measured as oxide), 10 milligrams of butylated hydroxy-toluene, 50 milligrams of vitamin E and 500 milligrams of sodium ascorbate. A completed capsule was taken daily by an adult human.

EXAMPLE 7

One hundred twenty $ARS/BDF_1$ random bred mice were obtained one month after weaning; they had been raised on a standard nutritionally adequate control diet.

The mice were divided into three equal groups, the first group, of forty mice being labeled test diet group 1, the second group of forty mice being labeled test diet group 2, and the third group of forty mice being labeled the control diet group.

The control diet group was fed standard diet no. 1 which consists of:

|  | g/kg |
|---|---|
| INGREDIENTS |  |
| Casein, vitamin free | 200.00 |
| Glucose, monohydrate | 654.00 |
| Corn Oil, tocopherol stripped | 100.00 |
| Salt mix, Gen. Biochem. J. No. 4164 | 40.00 |
| Vitamin mix (see below) | 6.00 |
| VITAMIN MIX |  |
| Biotin | 0.0001 |
| Vitamin $B_{12}$ | 0.0001 |
| Calcium pantothenate | 0.0100 |
| Choline chloride | 1.000 |
| Folic acid | 0.001 |
| Menadione $NaHSO_4$ | 0.001 |
| Nicotine acid | 0.025 |
| Pyridoxine HCl | 0.025 |
| Riboflavine | 0.005 |
| Thiamine | 0.005 |
| Tocopherol | 0.001 |
|  | units/kg |

-continued

| | |
|---|---|
| Vitamin A | 25,000 |
| Vitamin D | 2,000 |

The control diet was a chemically defined diet which normally is used as a standard procedure for studies with mice. The control diet was commerically available as shown, and corresponds to TD-71046 which has the same formula as that for Catalog #170290, except that vitamin E acetate was added in the amount of 132.0 IU/kg of diet at the expense of carbohydrate. The casein ingredient of standard diet No. 1 contained the natural and normal concentration of sulfur-containing amino acids found in all such chemically defined laboratory animal diets. This is shown by page 216 of *The Merck Index,* 8th Edition (1968). The control diet (standard diet No. 1) contained nutritionally adequate amounts of vitamin E, selenium and sulfur-containing amino acids. The mice synthesize all of their nutritional requirements for ascorbic acid (vitamin C). The control diet (standard diet No. 1) has been found to be more than nutritionally adequate for lifespan and all laboratory experiments. The control diet contains more than minimum nutrients—it contains a recommended daily allowance plus an excess to provide healthy laboratory animals.

At the same time, test diet group 1 was fed test diet No. 2, which consists of standard diet No. 1 plus 500 I.U. of vitamin E (added as alpha tocopheryl acetate), 300 milligrams of vitamin C (added as ascorbic acid), 300 micrograms of butylated hydroxy-toluene, 25 milligrams of cysteine (from soybeans) and 15 micrograms of selenium (measured as oxide) per 120 pounds of body weight per daily intake.

Also at the same time, test diet group 2 was fed test diet No. 3, which consists of standard diet No. 1, having the tocopherol (vitamin E) stripped therefrom. Test diet No. 3 which was identical to standard diet No. 1 except that it was stripped of the vitamin E (tocopherol) content. Thus, test diet No. 3 is identical to the vitamin deficient test diet (Catalog # 170290).

The diets used in the entire experiment thus contained the essential ingredients of this invention as follows:

(a) Standard diet No. 1 contained sulfur-containing amino acid (in the casein), vitamin E (tocopherol) in an amount of 0.001 g/kg, and selenium in a nutritionally adequate amount.

(b) Test diet No. 2 contained sulfur-containing amino acids (in the casein) plus additional vitamin E (500 I.U.) plus additional sulfur-containing amino acid (25 mg. cysteine) plus added selenium (15 micrograms measured as oxide) plus 300 mg vitamin C plus 300 micrograms BHT per 120 pounds of body weight per daily intake.

(c) Test diet No. 3 contained sulfur-containing amino acids (in the casein) but had no tocopherol (vitamin E) content.

Regarding the selenium content of standard diet No. 1, there is no presently established minimum daily requirement (nutritionally adequate amount) of selenium for either animals or humans. Selenium occurs naturally in varying amounts in a wide variety of foods and also is present as an impurity in the preferred sulfur-containing amino acids. In this experiment, with vitamin C and the other antioxidant held constant, the other three essential ingredients are interrelated, one sometimes being able to substitute for another for one or more purposes, e.g., for the prevention of liver necrosis and musciar dystrophy. Therefore, with each varying amount of the other two essential ingredients, i.e., sulfur-containing amino acid and vitamin E, a different quantity of selenium would be considered minimal. The only true test to determine whether a minimum daily requirement or nutritionally adequate amount of any one or all of the essential ingredients is present is to check for deficiency diseases (e.g., liver necrosis). There was no liver necrosis or other gross abnormality in any of the mice tested including all of those fed standard diet No. 1. Therefore, it is concluded that the trace amounts of selenium naturally contained in one or more of the ingredients of said standard diet No. 1 was sufficient to supply the nutritionally adequate amount, especially in the presence of the relatively large amounts of vitamin E (tocopherol) and sulfur containing amino acids contained in the diet. The presence of selenium, per se, is not a normal or ordinary standard in determining the adequate nutrition of a laboratory diet. (Purina Laboratory Chow is a standard laboratory diet for raising healthy, normal laboratory animals, such as, mice and rats—selenium is not separately listed as being present in such a formulation.)

Half of the control diet group of mice and half of each test diet group of mice were placed in, and kept in, a first environmental room during the period in which they were being fed the above-described diets. The other halves of the three groups of mice were placed in, and kept in, a second environmental room during the period in which they were being fed the above-described diet. Each mouse was tagged and fed only the assigned diet. The two environmental rooms had controlled and equal air flows, light cycles and temperatures.

The lifespan of each mouse was recorded. Many of the mice were autopsied, and all of the autopsies showed normal deaths with no gross abnormalities.

The lifespan of the control diet group followed a typical distribution curve for their specie. The mice of that group in each environmental room experienced the same lifespan distribution. The data obtained and the number of mice used in that group was statistically significant.

The mean lifespan of test diet group 1 of mice (receiving the essential ingredients of the present invention) showed a mean lifespan increase of 66 percent when compared to the mean lifespan of the control diet group of mice. The maximum lifespan of any mouse in test diet group 1 showed a maximum life increase of 20 percent when compared to the maximum lifespan of any mouse in the control diet group of mice. This shows a synergistic improvement in lifespan by retardation of the aging process.

The lifespan of test diet group 1 followed a typical distribution curve for their specie (only vastly longer than the curve for the control diet group). The mice of that group in each environmental room experienced the same lifespan distribution. The data obtained and the number of mice used in that group was statistically significant.

Calculations made of the increased antioxidant activity of standard diet No. 1 over that of test diet No. 3 (vitamin E removed) indicated a projected lifespan increase approaching 10 percent from the antioxidants contained in test diet No. 2.(corresponding to this invention). The 66 percent increase in lifespan actually obtained with mice fed test diet No. 2 is due to the synergism of this invention.

Gross toxicity studies of test diet No. 2 indicated no detrimental effects or toxicity to the mice.

Routine checks for liver necrosis as well as all liver and other organ abnormalities by autopsy at death after testing was done. Pathological reports from an independent testing laboratory were made. Only two mice were found to have liver abnormalities, one a mottled liver and one an enlarged liver. These abnormalities were not considered to be gross abnormalities.

The comparative tests of the experiments set forth above establish that synergistic increases of the mean lifespan and the maximum lifespan of laboratory test mice were obtained by the use of the claimed combination of antioxidants (BHT, vitamin C, vitamin E), selenium and a sulfur-containing-amino acid (cysteine) eat the claimed level and proportions. These synergistic increases were totally unexpected in view of the prior art.

EXAMPLE 8

21 eight-month old C57/BL/6 strain of inbred mice were obtained. The mice had been raised on a standard diet. The mice were divided into three equal groups; one group being labeled the control diet group, one group being labeled the enriched control diet group, and one group being labeled the invention diet group.

The control diet group was fed standard diet No. 1 for five days. Standard diet No. 1 was identical to the standard diet No. 1 of Example 7.

At the same time, the enriched control diet group was fed enriched standard diet No. 1 for five days. Enriched standard diet No. 1 consisted of standard diet No. 1 plus 150 milligrams of vitamin E acetate per 120 lbs of body weight per daily intake (the amount of glucose monohydrate being lowered by a corresponding amount in order to maintain the other kg ratios in the levels in standard diet No. 1).

At the same time, the invention diet group was fed invention diet No. 1 for five days. Invention diet No. 1 consisted of standard diet No. 1, plus the antioxidant portion of this invention (350 I.U. of vitamin E, 300 milligrams of ascorbic acid and 300 micrograms of butylated hydroxytoluene per 120 lbs. of body weight per daily intake), even though mice produce all of the ascorbic acid they need for nutritional purposes.

The effects of the five components of this invention can be broken down into immediate and long term effects. Immediate effects are governed by the antioxidant effect and long term effects by the enzyme activity and antibody production of the immune system as discussed previously. This is so because the antioxidant effect is mainly preventative, while the enzyme activity and antibody production effects are restorative and destructive, respectively, of what was not prevented.

Acute toxicity from lethal concentrations of air pollution or ingestion of a toxic substance is obviously an immediate effect, while cancer and an increased rate of aging are obviously long term effects. The latent period in humans for cancer is generally recognized as being as long as up to 20 years. To study the preventative effect, only the antioxidant portion was used since the test was designed to be lethal immediately, with no value to the long term effects for experimental purposes. For other than experimental research purposes, it would be ridiculous to protect an animal from short term effects and know that the animal's long term future would be shortened by the agony of cancer and by the painful incapacitation of other diseases caused by the toxic substance administered.

Each mouse of the control diet group was individually placed in (isolated in) a sealed environmental test chamber which contained a controlled atmosphere, which was reproduced (the same) each test. The controlled atmosphere contained, among other things, constant starting levels of pure oxygen and oxidizing air pollutants commonly found in automotive exhausts. The known oxidizing air pollutants in the controlled atmosphere were $N_2O$, $NO_2$, various aromatic hydrocarbons and $CO_2$. The time from placing each mouse in the chamber until the death of each mouse was recorded. The surival time of the control diet group, obtained as individuals fell within the Gaussian distribution curve. The average value survival time for the control diet group and their standard deviation are as follows:

Control Standard Diet Group: 75 seconds (Other mice of a natural control diet group had previously been used to conduct tests to determine adequate oxygen levels, see Example 11.)

Each mouse of the enriched diet group was individually placed in (isolated in) a sealed environmental test chamber which contained a controlled atmosphere, which was reproduced (the same) each test. The controlled atmosphere contained, among other things, constant starting levels of pure oxygen and oxidizing air pollutants commonly found in automotive exhausts. The known oxidizing air pollutants in the controlled atmosphere were $N_2O$, $NO_2$, various aromatic hydrocarbons and $CO_2$. The time from placing each mouse in the chamber until the death of each mouse was recorded. The survival time of the enriched control diet group, obtained as individuals, fell within the Gaussian distribution curve. The average value survival time for the enriched control diet group and their standard deviation are as follows:

Enriched Standard Diet Group: 217+19 seconds

Each mouse of the invention diet group was individually placed in the sealed environmental test chamber, being alternated with mice from the standard diet and enriched standard diet group. A controlled atmosphere having the same ingredients described above was used each time. The time from placing each mouse in the chamber until the death of each mouse was recorded. The survival time of the invention diet group, obtained as individuals, fell within the Gaussian distribution curve. The average value survival time for the invention diet group and their standard deviation are as follows:

Invention Diet Group: 370+7.8 seconds

The mice of the invention diet group showed a synergistic improvement over the mice of the enriched standard diet group of 71 percent in survival time in the oxidizing air pollutant atmosphere. The mice of the invention diet-group showed a synergistic improvement over the mice of the standard diet group of 493 percent in survival time in the oxidizing air pollutant atmosphere.

Liver necrosis, as well as all liver and organ abnormalities, were routinely checked for and no incidence of any statistical significance was found.

The control diet used in these tests was a chemically-defined diet for mice studies, and was commerically available. The caesin contains the natural and normal concentrations of sulfur-containing amino acids found in all such chemically-defined commercially available diets.

The comparative test results of this example establish that synergistic protection against common oxidizing air pollutants is obtained by the use of the antioxidant portion of this invention. This synergistic protection is totally unexpected in view of the prior art.

EXAMPLE 9

The experiment of Example 8 was repeated using three separate strains of mice. Fifteen mice in each strain were divided into three groups of five mice each. One group from each of the three strains of mice were fed standard diet No. 1 (same as that of Example 8) for two weeks; one group from each of the three strains of mice were fed enriched standard diet No. 1 (same as that of Example 8) for two weeks; and one group from each of the three strains of mice were fed invention diet No. 1 (same as that of Example 8) for two weeks. Although survival times varied for each strain of mice, the mice fed invention diet No. 1 had an average value survival time increase of about 200 percent ober the mice fed enriched standard diet No. 1.

The comparative test results in this example establish that synergistic protection against common oxidizing air pollutants is obtained by the use of the antioxidant portion of this invention. This synergistic protection is totally unexpected in view of the prior art. Also, the comparative test results show that the synergistic protection increases with the length of use of the antioxidant portion the novel food and feed supplement of this application.

EXAMPLE 10

Several ARS/DBF$_2$ strain of mice were obtained. The mice had been raised on a standard diet.

The sealed environmental test chamber described in Example 8 was purged several times with pure nitrogen. Then enough oxygen was introduced to raise the oxygen level to that used in the experiments described in Example 8. The mice were introduced into the environmental test chamber.

The mice appeared to be comfortable and their behavior was normal. After 1305 seconds all of the mice were removed from the chamber. None of the mice had died during the test and none of the mice appeared to have any adverse effects.

The length of the test described just above was at least six times the average value survival time of the enriched control diet group of mice and was at least three times the average value survival time of the invention diet group of mice.

These tests demonstrated that the oxygen level in the sealed environmental test chamber in Example 8 was more than sufficient to sustain life (mice) at comfortable levels for several times the length of the tests of Example 8. Or, in other words, the test set forth in Example 8 were conducted with sufficient levels and amounts of oxygen so that those factors did not effect the survival time of the test mice in Example 8.

EXAMPLE 11

Six ARS/BDF$_1$ strain mice were obtained. The mice had been raised on a standard diet (Wayne diet blocks-natural). The six mice were divided into two equal groups. In each group, one mouse was fed enriched standard diet No. 1 (same as that of Example 8) and termed the enriched standard diet mouse. In each group, a second mouse was fed invention diet No. 1 (same as that of Example 8) and termed invention diet mouse. In each group, the third mouse was fed a diet which was deficient in certain known, required ingredients for mice diet, and termed the deficient diet mouse. All six mice were kept on their respective diet for 41 days.

The mice in one group were all placed in the sealed environmental test chamber (described in Example 8) which contained a controlled atmosphere, which was identical to the one described in Example 8. The time from placing the mice in the chamber until the death of each mouse was recorded. The enriched standard diet mouse and the deficeint diet mouse died first. The invention diet mouse lived much longer than theother two mice; the invention diet mouse lived 201 percent longer than the enriched standard diet mouse.

The mice in the other group were all placed in the same sealed environmental chamber atmosphere. The test was conducted in the same manner. The enriched standard diet mouse and the deficient diet mouse died first. The invention diet mouse lived much longer than the other two mice; the invention diet mouse lived 175 percent longer than the enriched standard diet mouse.

EXAMPLE 12

Three C57/BL/6N strain mice were obtained. The mice had been raised on a standard diet. One mouse was fed enriched standard diet No. 1 (same as that of Example 8) and termed the enriched diet mouse. The second mouse was fed invention diet No. 1 (same as that of Example 8) and termed the invention diet mouse. The third mouse was fed a diet which was deficient in certain known, required ingredients for mice diets, and termed the deficient diet mouse. All three mice were kept on their respective diet for 30 days.

The mice were all placed in the sealed environmental test chamber (described in Example 8) which contained a controlled atmosphere, which was identical to the atmosphere described in Example 8. The time from placing the mice in the chamber until the death of each mouse was recorded. The enriched standard diet mouse and the deficient diet mouse died first. The invention diet mouse lived much longer than the other two mice; the invention diet mouse lived 211 percent longer than the enriched standard diet mouse.

EXAMPLE 13

Three DBA strain mice were obtained. The mice were raised on a standard diet. One mouse was fed enriched standard diet No. 1 (same as that of Example 8) and termed the enriched standard diet mouse. The second mouse was fed invention diet No. 1 (same as that of Example 8) and termed the invention diet mouse. The third mouse was fed; a diet which was deficient in certain known, required ingredients for mice diets, and termed the deficient diet mouse. All three mice were kept on their respective diets for 31 days.

The mice were placed in the sealed environmental test chamber (described in Example 8) which contained a controlled atmosphere, which was identical to the atmosphere described in Example 8. The time from placing the mice in the chamber until the death of each mouse was recorded. The enriched standard diet mouse and the deficient diet mouse died first. The invention diet mouse lived much longer than the other two mice; the invention diet mouse lived 223 percent longer than the enriched standard diet mouse.

The comparative test results in Examples 11, 12 and 13 further establish that synergistic protection against common oxidizing air pollutants is obtained by the use of the antioxidant portion of this invention and that the test results are not effected by or dependent upon one test group of mice or one strain of mice.

EXAMPLE 14

The main objective of this example was to simulate as closely as possible the maximum detrimental environmental factors, including known carcinogens and other pollutants which effect the quality and duration of human lives, on a test group of 12 female gerbils over their full lifespans. The gerbil was choosen because it is relatively free from disease and an active alert animal. Each gerbil was randomly marked. All carcinogens and their route of administration were choosen to most nearlyresemble, human conditions and then administered over several weeks to be maximized in potency. The five component food and feed supplement of this invention was prepared in two parts, an oil portion containing dimethyl selenide, BHA and ethoxyquin in d-alpha tocopheryl acetate and a solid portion containing the seleno, elemental and selenite forms of selenium with cysteine, methionine and ascorbic acid, and both were added to Purina Lab chow 5001 and administered in the first ½ gram of food each day at a dose intended to be $\frac{1}{100}$ of the compareable human dose. The remainder of the food and all water were available constantly.

The details of this example are as follows:

The test was conducted utilizing 12 female gerbils, born May 1, 1974, to May 6, 1974. The gerbils were randomly selected for inclusion in four groups. The four gerbils of Group I were given or exposed to various carcinogens as specified in detail below and were only fed a control diet of supplemented Purina Lab Chow 5001. The two gerbils of Group II were not fed or exposed to various carcinogens, and were only fed a control diet of supplemented Purina Lab Chow 5001. The four gerbils of Group III were given or exposed to various carcinogens as specified herein, and were fed a control diet of supplemented Purina Lab Chow 5001 containing the invention composition specified below. The two gerbils of Group IV were not fed or exposed to various carcinogens, and were fed a control diet of supplemented Purina Lab Chow 5001 containing the invention composition specified below. Group I (gerbils CN 1, 2, 3 and 4) was termed the carcinogen non-protected group; Group II (gerbils NN 1 and 2) was termed the non-carcinogen non-protected group; Group III (gerbils CP 1, 2, 3 and 4) was termed the carcinogen protected; and Group IV (gerbils NP 1 and 2) was termed the non-carcinogen protected.

The invention composition tested consisted of 3.59 $\mu$g of selenium (0.09, $\mu$g from selenocysteine and selenomethionine, 0.5 $\mu$g from sodium selenite, 1 $\mu$g from powdered selenium metal and 2 $\mu$g from dimethyl selenide), 250 $\mu$g of butylated hydroxy anisole, 250 $\mu$g of ethoxyquin, 1 mg of cysteine, 2 mg of methionine, 3 mg of d-alpha tocopheryl acetate and 7 mg of ascorbic acid daily in the control diet of supplemented Purina Purina Lab Chow 5001. From 6 to 8 weeks of age the gerbils were fed ⅓ of normal daily dose, from 8 to 10 weeks of age were fed ⅔ daily dose and full dose daily thereafter, plus 0.5 $\mu$g of Se in yeast (a new product purchased commercially Apr. 10, 1976) after the 2 year period.

Pollutants as indicated where not quantiatively measured, but were given with only two criteria for each pollutant; (1) that the amount used be similar to the approximate practical level that humans encounter at their maximum exposure, but (2) that the amount be well below the lowest lethal dose. Among pollutants used were about 10 which humans often encounter in daily life (asbestos, aerosal sprays, gasoline, pesticides, fungicides, vinyl chloride, chloroform, carbon tetrachloride, tetrachloroethane, tetrachloroethylene, trichloroethylene, formaldehyde, benzene and toluene). Cigarette smoke and some combustion engine exhaust (with all solids filtered out, dissolved in acetone, concentrated and added to food) were also used.

Some of the pollutants are also suspected as carcinogens, but are relatively less potent. Engine exhaust and cigarette smoke both contain benzopyrene in trace amounts (Ref: 1962, Cancer, Vol. 15, pages 95–107, states cigarette smoke contains 1.2 ppm of BP and exhaust about 35 $\mu$g of BP per minute for average auto). Known potent carcinogens were added to the food as indicated in the attached graph at 100 $\mu$g daily by a $\frac{1}{20}$ ml drop of carcinogen in solvent at 2 mg/ml concentration on ½ gram of control diet, except for arsenic. These carcinogens are among the most potent carcinogens known and, at the exposures used, each would separately normally be expected to cause cancer (or tumors or malignancies) at various sites in virtually all animals exposed thereto.

The quality and length of each gerbil's life was recorded. All of the gerbils were observed for activity on the exercise wheel, appearance of hair and brightness of eyes and any unusual factors. They were examined for palpable growths weekly. No autopsy or tissue analysis was performed. Gerbil weight and consumption of water and feed were not quantitatively measured at any time, only generally noted. This information is set out in the attached graph.

The following is a summary of important dates concerning the test (deaths not included);

| Date | Event |
|---|---|
| June 25, 1974 | Received gerbils, began ⅓ dose daily |
| July 1, 1974 | Increased protection to ⅔ dose daily |
| July 15, 1974 | Increased to full dose and began pollution nonquantitative; 2 criteria: common maximums and nonlethal. |
| August 5, 1974 | Combustion Exhaust and Cigarette smoke. Smoke from 10 cigarettes and then a portion of exhaust from auto engine run 30 sec., repeated 10 times per week for 6 weeks. Total of 30 packages of cigarettes plus 30 min. of exhaust, with gas portion mainly vented but solids collected, dissolved in acetone, concentrated and added to feed during 19th week only. |
| Sept. 23, 1974 | Began 7,12-dimethylbenzanthracene, acetone solvent; 100 $\mu$g of DMBA in food 5 days per week for 10 weeks; total of 5 mg of DMBA. |
| Dec. 16, 1974 | Began benzo (a) pyrene carcinogen; acetone solvent; 100 $\mu$g of BP in food 5 days per week for 20 weeks; total of 10 mg of BP. |
| May 26, 1975 | Began dimethylnitrosanime and on alternate days used diethylnitrosamine, water solvent for both; 100 $\mu$g of DMN or 100 $\mu$g of DEN on alternate days in food 5 days per week for 20 weeks; total of 5 mg of DMN plus 5 mg of DEN for a total of 10 mg of nitrosamines. |
| Nov. 10, 1975 | Began methylcholanthrene, acetone solvent; 100 $\mu$g of MCA in food 5 days per week for 10 weeks; total of 5 mg of MCA. |
| Feb. 23, 1976 | Began arsenic trioxide; 5 $\mu$g of arsenic trioxide in water, dropped in food on Monday and Thursday for 5 weeks; total of 50 $\mu$g of arsenic trioxide. Each time accompanied by inhalation of dimethyl selenide about equal to daily dietary dose. |
| May 3, 1976 | Commercial 0.5 $\mu$g of Se in yeast daily added. |
| Nov. 2, 1979 | Last gerbil died. |

The test results are set out in the following table:

TABLE

| Group | Gerbil | Died* | | Weeks of Lifespan from May 6, 1974 -Average- | General Quality of Life and Lifespan Ranking | Observations from Test |
|---|---|---|---|---|---|---|
| | Carcinogen Non-protected | | | | | |
| I | CN 2 | 4-11-75 | 48½ | 74⅞ or 75 weeks | Worst | Least active alert lives, dull eyes, poor hair, noticeable respiration problems, open lesions, multiple palpable growths and body distortions, Shortest lifespans from whatever cause. All gerbils in this group died before any in other groups. |
| | CN 3 | 8-24-75 | 67½ | | | |
| | CN 1 | 1-27-76 | 90 | | | |
| | CN 4 | 2-21-76 | 93 | | | |
| | Non-carcinogen Non-protected | | | | | |
| II | NN 1 | 4-14-78 | 205½ | 227¾ or 228 | Basis as controls | Wide variation, but with normal lifespan. Basis for relative comparison with all others. |
| | NN 2 | 2-19-79 | 250 | | | |
| | Carcinogen protected | | | | | |
| III | CP 3 | 7-15-78 | 218½ | 236⅞ or 237 | Better | Relatively more active alert lives. Similar or less problems during life. Equal or longer lifespans than controls. |
| | CP 1 | 10-23-78 | 233 | | | |
| | CP 4 | 12-6-78 | 239 | | | |
| | CP 2 | 1-10-79 | 257 | | | |
| | Non-carcinogen Protected | | | | | |
| IV | NP 2 | 3-11-79 | 252½ | 269½ or 270 | Best | Most active alert lives, bright eyes, least problems, glossy hair and probably heavier. Possibly less water consummed daily. Longest average and maximum lifespan. |
| | NP 1 | 11-2-79 | 286½ | | | |

Note: *Animals dead after Thursday morning of each week were given ½ week.

The data from the gerbil test shows an unexpected long increase in life span when fed the invention composition in the face of exposure to and consumption of large, prolonged amounts of various carcinogens. The gerbil group exposed to and fed carcinogens, but protected by the invention composition had a 216 percent increase in average lifespan over the gerbil group exposed to and fed carcinogens, but not protected by the invention composition.

$$\frac{237-75}{75} \times 100 = 216\%$$

This data shows the unobviousness and utility of the invention composition. Such carcinogen-exposed invention-protected group had a slightly longer average lifespan than the control group (non-exposed, non-protected group). The invention-protected group (non-exposed) even had a 18 percent increase in average lifespan over the control group.

$$\frac{270-228}{228} \times 100 = 18\%$$

Two other important observations were made from a qualitative standpoint, one impractical and the other very practical. First, during preliminary research tests it became apparent that the toxic dose level of chemicals is affected by the composition of this invention in such a way that high acute doses of toxic substances (both in the pollution and carcinogen catagory) which would be lethal without protection, were either completely non-lethal in the time observed or the time before death was greatly increased. Since it normally would be accidental to take an acute toxic dose of anything, this protection does not have wide spread practical significance except as a poison antidote, but remains interesting and definitely demonstrates the protective effect clearly. The cumulative effect of gradual protection from many toxic substances at various levels during a lifespan should definitely be a postive factor on both the quality and quantity of life. Although the biological mechanism of this protection is unknown, it could very well be the same mechanism which provides the beneficial effects of the composition of this invention at sub-toxic doses.

Second, but with immense practical significance, is the observation that, since the composition of this invention is capable of completely preventing the formation of all types of cancer, it also will prevent metastasis of existing cancer to other organs of the body. Therefore, surgery, chemothrapy and radiation, the current methods of cancer treatment, should be augmented with the protection of the composition of this invention to enhance the cure rate of current treatment. These current methods could remove or destroy the bulk of cancerous cells, leaving only a minute portion which in many people could manage to be eliminated completely by the body itself, with no metastesis, when protected by the composition of this invention. The quantitative implementation of this observation should be applied to humans immediately.

The five component food and feed supplement of this invention (i) is effective in retarding or delaying a substantial portion of the biological degradation normally associated with the aging process, (ii) will retard degradation of RNA synthetasis, prevent the accumulation of mis-synthesized RNA cells and protein in the body and increase the antibody reaction thereto, (iii) is effective in combating the aging accelerating effects of stress in all forms from the environment and stress related factors, (iv) is effective in reducing and/or delaying the accumulation of lipofuscin or age pigment in aging body cells, (v) increases the body's tolerance to radiation, which is both carcinogenic and age accelerating, and improves efficiency in utilizing oxygen, while reversing damage of epoxide and peroxide formation, (vi) aids in establishing and maintaining proper protein synthesis in the body which combats-both improper nitrogen balance and poor tissue replacement, (vii) inhibits free radical reactions in the body and rids the body of free radicals produced, and (viii) by the preceding mechanisms and effects, protects the body from environmental carcinogens and toxic pollutants (whether natural or man made), thereby improving both the quality and duration of human and animal life. It is important that all of these critical components be made available to the body simultaneously and continuously.

COMPONENT INFLUENCE

| Effect | Major | Minor and/or Supportive |
|---|---|---|
| Antioxidants in all types of cell media aqueous or lipid | Vitamin C Vitamin E Other Antioxidant Glutathione | Selenium is an antioxidant only in reduced form and present in only trace quantities, but then is an excellent antioxidant in direct reactions. Cysteine and methionine as precursors of glutathione. |
| Enzyme enhancement | Selenium Glutathione | All antioxidants by keepng selenium and glutathione in the reduced form necessary to function. Selenoamino acids as impurities from cysteine and methionine. |
| Immune or antibody production synergism | Selenium Vitamin E | Vitamin E and selenium mutually increase each others absorption by the body. Both cysteine and methionine lower the toxicity of selenite by conversion to dimethyl selenide. |

As can be seen from the above table, the five components are interwoven so that each is involved in at least two of the three effects described. This interweaving provides unexpectedly, but logically, strong synergism, since all three effects must take place for optimum results and within the immune effect the synergism is such that 1 plus 7 equals 35 in antibody production. The multiple and varied antioxidants assure that the antioxidant effect occurs in all types of cell media and that selenium and glutathione, remain in the reduced form in which they must be present to be effective. Any one of the five components alone will have some undetermined value and the synergism increases to the optimum when all five components are concurrently available. Since dimethyl selenide is eliminated from the body within a fraction of a day, the other forms of selenium assure that more dimethyl selenide is produced by the body and available continuously for greater than a day.

What is claimed is:

1. A five component food and feed supplement consisting essentially of:
   (a) water soluble antioxidant vitamin C, or ascorbic acid, or any of its forms or derivatives, or mixtures thereof,
   (b) oil soluble antioxidant vitamin E, or alpha-tocopherol, or any of its forms or derivatives, or mixtures thereof,
   (c) the element selenium, or a chemical or composition containing it, or mixtures thereof,
   (d) a sulfur amino acid, in any form, or a sulfur peptide, or a sulfur protein, or any of their derivatives, or mixtures thereof, and
   (e) another antioxidant, other than vitamin C and other than vitamin E, which is synthetic or natural and water soluble or oil soluble, or a mixture of such antioxidants, or a combination of such forms thereof.

2. The food and feed supplement as claimed in Claim 1 which consists essentially of:
   (a) ascorbic acid,
   (b) d-alpha-tocopheryl acetate,
   (c) sodium selenite, elemental selenium, selenomethionine, selenocysteine, and potassium selenide providing selenium in all oxidation states for continuous availability,
   (d) glutathione, methionine and cysteine, and
   (e) butylated hydroxy anisole and ethoxyguin.

3. The food and feed supplement as claimed in claim 1 wherein the total weight, on a ratio basis, of each of the five components, including all of the forms or mixtures thereof, is:
   (i) from 1 milligram to 50 grams of component (a),
   (ii) from 1 milligram to 20 grams of component (b),
   (iii) from 5 micrograms to 20 grams of component (c),
   (iv) from 1 milligram to 20 grams of component (d),
   (v) from 5 micrograms to 20 grams of component (e).

4. The food and feed supplement as claimed in claim 2 wherein the total weight, on a ratio basis, of each of the five components, including all of the forms or mixtures thereof, is:
   (i) from 1 milligram to 50 grams of component (a),
   (ii) from 1 milligram to 20 grams of component (b),
   (iii) from 5 micrograms to 20 grams of components (c),
   (iv) from 1 milligram to 20 grams of components (d),
   (v) from 5 micrograms to 20 grams of components (e).

5. A pharmaceutically acceptable dosage form comprising 1) elemental selenium; 2) a sulfur amino acid, in any form, a sulfur peptide, a sulfur protein, or any of their derivatives or mixtures thereof; and 3) a pharmaceutically acceptable carrier.

6. The dosage form of claim 5 which comprises about 5 $\mu$g–20 g of said selenium.

7. The dosage form of claim 5 which comprises about 50 $\mu$g–500 g of said selenium.

8. A pharmaceutically acceptable dosage form comprising 1) an organic selenium compound; 2) a sulfur amino acid, in any form, a sulfur peptide, a sulfur protein, or any of their derivatives or mixtures thereof; and 3) a pharmaceutically acceptable carrier.

9. The dosage form of claim 8 wherein the organic selenium compound is a selenide.

10. The dosage form of claim 8, which comprises about 5 $\mu$g–20 g of said organic selenium compound.

11. The dosage form of claim 8 which comprises about 50 $\mu$g–500 $\mu$g of said organic selenium compound.

12. The dosage form of claim 8 wherein the compound is selenoglutathione.

13. A pharmaceutically acceptable dosage form comprising 1) an inorganic selenium compound; 2) a sulfur amino acid, in any form, a sulfur peptide, a sulfur protein, or any of their derivatives or mixtures thereof; and 3) a pharmaceutically acceptable carrier.

14. The dosage form of claim 13, which comprises about 5 μg–20 g of said inorganic selenium compound.

15. The dosage form of claim 13, which comprises about 50 μg–500 μg of said inorganic selenium compound.

16. A composition comprising 1) elemental selenium, 2) vitamin E, or alpha-tocopherol, or any of its forms or derivatives, or mixtures thereof, and 3) a sulfur amino acid, in any form, a sulfur peptide, a sulfur protein, or any of their derivatives or mixtures thereof.

17. A composition comprising 1) an organic selenium compound, 2) vitamin E, or alpha-tocopherol, or any of its forms or derivatives, or mixtures thereof, and 3) a sulfur amino acid, in any fonn, a sulfur peptide, a sulfur protein, or any of their derivatives or mixtures thereof.

18. A composition comprising 1) an inorganic selenium compound, 2) vitamin E, or alpha-tocopherol, or any of its forms or derivatives, or mixtures thereof, and 3) a sulfur amino acid, in any form, a sulfur peptide, a sulfur protein, or any of their derivatives or mixtures thereof.

19. The composition of claim 16, 17, or 18 further comprising one or more other antioxidants.

20. The composition of claims 16, 17, or 18 comprising at least 5 μg of the elemental selenium or the selenium compound.

21. The composition of claims 16, 17, or 18 comprising 50 μg to 500 μg of the elemental selenium or the selenium compound.

22. A pharmaceutical composition comprising 1) elemental selenium, 2) water soluble antioxidant vitamin C, or ascorbic acid, or any of its forms or derivatives or mixtures thereof, and 3) a pharmaceutically acceptable carrier.

23. A pharmaceutical composition comprising 1) an organic selenium compound, 2) water soluble antioxidant vitamin C, or ascorbic acid, or any of its forms or derivatives or mixtures thereof, and 3) a pharmaceutically acceptable carrier.

24. A pharmaceutical composition comprising 1) an inorganic selenium compound, 2) water soluble antioxidant vitamin C, or ascorbic acid, or any of its forms or derivatives or mixtures thereof, and 3) a pharmaceutically acceptable carrier.

25. A composition comprising 1) elemental selenium, 2) vitamin E, or pha-tocopherol, or any of its forms or derivatives, or mixtures thereof, and 3) vitamin C (ascorbic acid), or any of its forms or derivatives or mixtures thereof.

26. A composition comprising 1) an organic selenium compound, 2) vitamin E, or alpha-tocopherol, or any of its forms or derivatives, or mixtures thereof, and 3) vitamin C (ascorbic acid), or any of its forms or derivatives or mixtures thereof.

27. A composition comprising 1) an inorganic selenium compound, 2) vitamin E, or alpha-tocopherol, or any of its forms or derivatives, or mixtures thereof, and 3) vitamin C (ascorbic acid), or any of its forms or derivatives or mixtures thereof.

28. The composition of claim 16, 17, 18, 25, 26, or 27, further comprising a pharmaceutically acceptable carrier.

29. The composition of claim 25, 26, or 27, comprising at least 5 μg of the elemental selenium or the selenium compound.

30. The composition of claims 25, 26, or 27, comprising 50 μg to 500 μg of the elemental selenium or the selenium compound.

31. The composition of claim 28 comprising at least 5 μg of the elemental selenium or the selenium compound.

32. The composition of claim 28, comprising 50 μg to 500 μg of the elemental selenium or the selenium compound.

33. A composition comprising 1) elemental selenium, and 2) an antioxidant comprising a disulfide bond.

34. A composition comprising 1) an organic selenium compound, and 2) an antioxidant comprising a disulfide bond.

35. A composition comprising 1) an inorganic selenium compound, and 2) an antioxidant comprising a disulfide bond.

36. The composition of claim 33, 16, or 35 further comprising vitamin E, or alpha-tocopherol, or any of its forms or derivatives, or mixtures thereof.

37. The composition of claim 33, 16, or 35 further comprising a sulfur amino acid, in any form, a sulfur peptide, a sulfur protein, or any of their derivatives or mixtures thereof.

38. The composition of claim 36 further comprising a sulfur amino acid, in any form, a sulfur peptide, a sulfur protein or any of their derivatives or mixtures thereof.

39. The composition of claim 33, 34, or 35, further comprising a pharmaceutically acceptable carrier.

40. The composition of claim 36, further comprising a pharmaceutically acceptable carrier.

41. The composition of claim 37, further comprising a pharmaceutically acceptable carrier.

42. The composition of claim 38, further comprising a pharmaceutically acceptable carrier.

43. The composition of claim 33, 34, or 35 comprising at least 5 μg of the elemental selenium or the selenium compound.

44. The composition of claims 33, 34, or 35, comprising 50 μg to 500 μg of the elemental selenium or the selenium compound.

45. The composition of claim 39 comprising at least 5 μg of the elemental selenium or the selenium compound.

46. The composition of claim 39, comprising 50 μg to 500 μg of the elemental selenium or the selenium compound.

47. A method of protecting a host from the harmful physiological effects of one or more chemical carcinogens and/or pollutants present in the environment which comprises the repeated administration to said host of an effective amount of the element selenium or a compound containing selenium, wherein said selenium or selenium compound is in a pharmaceutically acceptable dosage form.

48. The method of claim 47 wherein an inorganic selenium compound is administered.

49. The method of claim 47 wherein an organic selenium compound is administered.

50. The method of claim 49 wherein the organic selenium compound comprises a seleno amino acid.

51. The method of claim 50 wherein the amino acid comprises selenomethionine or selenocysteine.

52. The method of claim 49 wherein a selenide is administered.

53. The method of claim 52 wherein the selenide comprises dimethyl selenide.

54. The method of claim 48 wherein sodium selenite or potassium selenide is administered.

55. The method of claim 47 wherein a volatile form of the selenium or selenium compound is administered.

56. The method of claim 47 further comprising administering vitamin E, or alpha-tocopherol, or any of its forms or derivatives or mixtures thereof.

57. The method of claim 47 further comprising administering a sulfur amino acid, in any form, a sulfur peptide, a sulfur protein, or any of their derivatives or mixtures thereof.

58. The method of claim 47 further comprising administering an antioxidant, other than vitamin C and other than vitamin E.

59. The method of claim 47 wherein the administration is oral.

60. The method of claim 47 wherein the host is a human.

61. The method of claim 47 further comprising administering:
   (a) ascorbic acid, its derivatives, or mixtures thereof,
   (b) oil-soluble antioxidant vitamin E, or alpha-tocopherol, or any of its forms or derivatives, or mixtures thereof,
   (c) a sulfur amino acid, in any form, a sulfur peptide, a sulfur protein, or any of their derivatives or mixtures thereof,
   (d) another antioxidant, other than vitamin C and other than vitamin E.

62. The method of claim 47 comprising administering:
   (a) ascorbic acid,
   (b) d-alpha-tocopheryl acetate,
   (c) sodium selenite, elemental selenium, selenomethionine, selenocysteine, or potassium selenide,
   (d) glutathione, methionine or cysteine, and (e) butylated hydroxy anisole, butylated hydroxytoluene or ethoxyquin.

63. The method of claim 47 wherein the compound is selenoglutathione.

64. A method of reducing the incidence of one or more cancers sensitive to the effects of an organic selenium compound, which comprises administering to a host at risk of developing said one or more cancers an effective cancer incidence-reducing amount of the organic selenium compound.

65. A method of inhibiting metastasis of cancer cells sensitive to the effects of an organic selenium compound which comprises administering to a host in need of such inhibiting, a metastasis-inhibiting amount of the organic selenium compound.

66. The method of claim 65, wherein said host is undergoing a treatment for cancer selected from the group consisting of surgery, radiation and chemotherapy.

67. The method of claim 64 or 65 wherein the organic selenium compound comprises a seleno amino acid.

68. The method of claim 67 wherein the amino acid comprises selenomethionine or selenocysteine.

69. The method of claim 64 or 65 wherein a selenide is administered.

70. The method of claim 69 wherein the selenide comprises dimethyl selenide.

71. The method of claim 64 or 65 wherein a volatile organic selenium compound is administered.

72. The method of claim 64 or 65 further comprising administering vitamin E, or alpha-tocopherol, or any of its forms or derivatives, or mixtures thereof.

73. The method of claim 64 or 65 further comprising administering a sulfur amino acid, in any form, a sulfur peptide, a sulfur protein, or any of their derivatives or mixtures thereof.

74. The method of claim 64, or 65 further comprising administering an antioxidant, other than vitamin C and other than vitamin E.

75. The method of claim 64 or 65 wherein the administration is oral.

76. The method of claim 64 or 65 wherein the host is a human.

77. The method of claim 64 or 65 further comprising administering:
   (a) ascorbic acid, its derivatives, or mixtures thereof,
   (b) oil-soluble antioxidant vitamin E, or alpha-tocopherol, or any of its forms or derivatives, or mixtures thereof,
   (c) a sulfur amino acid, in any form, a sulfur peptide, a sulfur protein, or any of their derivatives or mixtures thereof, and
   (d) another antioxidant, other than vitamin C and other than vitamin E.

78. The method of claim 64 or 65 comprising administering:
   (a) ascorbic acid,
   (b) d-alpha-tocopheryl acetate,
   (c) selenomethionine or selenocysteine,
   (d) glutathione, methionine or cysteine, and
   (e) butylated hydroxy anisole, butylated hydroxytoluene or ethoxyquin.

79. The method of claim 64 or 65 wherein the compound is selenoglutathione.

80. A method of reducing the incidence of one or more cancers sensitive to the effects of an inorganic selenium compound, which comprises administering to a host at risk of developing said one or more cancers an effective cancer incidence-reducing amount of said inorganic selenium compound, wherein the ratio of oxygen atoms to selenium atoms in the inorganic selenium compound is less than six.

81. A method of inhibiting metastasis of cancer cells sensitive to the effects of an inorganic selenium compound, which comprises administering to a host in need of such inhibiting, a metastasis-inhibiting amount of said inorganic selenium compound, wherein the ratio of oxygen atoms to selenium atoms in the inorganic selenium compound is less than six.

82. The method of claim 81, wherein said host is undergoing a treatment for cancer selected from the group consisting of surgery, radiation and chemotherapy.

83. The method of claim 80 or 81 wherein a selenide is administered.

84. The method of claim 80 or 81 wherein sodium selenite or potassium selenide is administered.

85. The method of claim 80 or 81 wherein a volatile form of the inorganic selenium compound is administered.

86. The method of claim 80 or 81 further comprising administering vitamin E, or alpha-tocopherol, or any of its forms or derivatives, or mixtures thereof.

87. The method of claim 80 or 81 further comprising administering a sulfur amino acid, in any form, a sulfur peptide, a sulfur protein, or any of their derivatives or mixtures thereof.

88. The method of claim 80 or 81 further comprising administering an antioxidant, other than vitamin C and other than vitamin E.

89. The method of claim 80 or 87 wherein the administration is oral.

90. The method of claim 80 or 81 wherein the host is a human.

91. The method of claim 80 or 81 further comprising administering:
   (a) ascorbic acid, its derivatives, or mixtures thereof,
   (b) oil-soluble antioxidant vitamin E, or alpha-tocopherol, or any of its forms or derivatives, or mixtures thereof,
   (c) a sulfur amino acid, in any form, a sulfur peptide, a sulfur protein, or any of their derivatives or mixtures thereof, and
   (d) another antioxidant, other than vitamin C and other than vitamin E.

92. The method of claim 80 or 81 comprising administering:
(a) ascorbic acid,
(b) d-alpha-tocopheryl acetate,
(c) sodium selenite or potassium selenide,
(d) glutathione, methionine or cysteine, and
(e) butylated hydroxy anisole, butylated hydroxytoluene or ethoxyquin.

93. A method of reducing the incidence of one or more cancers sensitive to the effects of elemental selenium, which comprises administering to a host at risk of developing said one or more cancers an effective cancer incidence-reducing amount of elemental selenium.

94. A method of inhibiting metastasis of cancer cells sensitive to the effects of elemental selenium, which comprises administering to a host in need of such inhibiting, a metastasis-inhibiting amount of elemental selenium.

95. The method of claim 94, wherein said host is undergoing a treatment for cancer selected from the group consisting of surgery, radiation and chemotherapy.

96. The method of claim 93 or 94 further comprising administering vitamin E, or alpha-tocopherol, or any of its forms or derivatives, or mixtures thereof.

97. The method of claim 93 or 94 further comprising administering a sulfur amino acid, in any form, a sulfur peptide, a sulfur protein, or any of their derivatives or mixtures thereof.

98. The method of claim 93 or 94 further comprising administering an antioxidant, other than vitamin C and other than vitamin E.

99. The method of claim 93 or 94 wherein the administration is oral.

100. The method of claim 93 or 94 wherein the host is a human.

101. The method of claim 93 or 94 further comprising administering:
(a) ascorbic acid, its derivatives, or mixtures thereof,
(b) oil-soluble antioxidant vitamin E, or alpha-tocopherol, or any of its forms or derivatives, or mixtures thereof,
(c) a sulfur amino acid, in any form, a sulfur peptide, a sulfur protein, or any of their derivatives or mixtures thereof, and
(d) another antioxidant, other than vitamin C and other than vitamin E.

102. The method of claim 93 or 94 comprising administering:
(a) ascorbic acid,
(b) d-alpha-tocopheryl acetate,
(c) elemental selenium,
(d) glutathione, methionine or cysteine, and
(e) butylated hydroxy anisole, butylated hydroxytoluene or ethoxyquin.

103. A method comprising repairing DNA, RNA, or a protein damaged by epoxide formation by contacting the DNA, RNA, or protein with an amount of the element selenium or a selenium compound effective to convert the epoxide to a double bond.

104. The method of claim 103 wherein DNA is repaired.

105. The method of claim 103 wherein RNA is repaired.

106. The method of claim 103 wherein a protein is repaired.

107. The method of claim 103 wherein the selenium compound is an inorganic selenium compound.

108. The method of claim 103 wherein the selenium compound is an organic selenium compound.

109. The method of claim 108 wherein the organic selenium compound comprises a seleno amino acid.

110. The method of claim 109 wherein the amino acid comprises selenomethionine or selenocysteine.

111. The method of claim 103 wherein the selenium compound is a selenide.

112. The method of claim 111 wherein the selenide comprises dimethyl selenide.

113. The method of claim 103 wherein the compound is sodium selenite or potassium selenide.

114. The method of claim 103 wherein the compound is selenoglutathione.

115. The method of claim 103 wherein the damage results from a reaction initiated by a free radical.

116. The method of claim 103 wherein the repair of DNA or RNA prevents the mis-synthesis of a protein.

* * * * *